US011334328B1

(12) United States Patent
Melvin et al.

(10) Patent No.: US 11,334,328 B1
(45) Date of Patent: May 17, 2022

(54) SYSTEMS AND METHODS FOR GENERATING INTERACTIVE HYPERMEDIA GRAPHICAL USER INTERFACES ON A MOBILE DEVICE

(71) Applicant: TeleTracking Technologies, Inc., Pittsburgh, PA (US)

(72) Inventors: Shawn Melvin, Pittsburgh, PA (US); Jason Spector, Pittsburgh, PA (US); Jason Harber, Pittsburgh, PA (US)

(73) Assignee: TeleTracking Technologies, Inc., Pittsburgh, PA (US)

( * ) Notice: Subject to any disclaimer, the term of this patent is extended or adjusted under 35 U.S.C. 154(b) by 0 days.

(21) Appl. No.: 17/011,559

(22) Filed: Sep. 3, 2020

Related U.S. Application Data

(63) Continuation of application No. 15/798,609, filed on Oct. 31, 2017, now Pat. No. 10,768,910.

(60) Provisional application No. 62/415,127, filed on Oct. 31, 2016.

(51) Int. Cl.
*G06F 8/38* (2018.01)
*G06F 16/955* (2019.01)
*G16H 40/20* (2018.01)
*G06F 3/0481* (2022.01)
*G06F 9/451* (2018.01)
*H04M 1/72448* (2021.01)

(52) U.S. Cl.
CPC .............. *G06F 8/38* (2013.01); *G06F 3/0481* (2013.01); *G06F 9/451* (2018.02); *G06F 16/9558* (2019.01); *G16H 40/20* (2018.01); *H04M 1/72448* (2021.01)

(58) Field of Classification Search
CPC ...... G06F 8/38; G06F 16/9558; G06F 16/954; G06F 3/0481; G06F 3/482; G16H 40/20; H04M 1/72448; H04M 1/724
USPC ........................................................ 715/763
See application file for complete search history.

(56) References Cited

U.S. PATENT DOCUMENTS

| 7,457,262 B1 * | 11/2008 | Doshi ................... H04W 24/04 |
| | | 370/328 |
| 7,467,163 B1 * | 12/2008 | Dodds ................. G06F 16/2458 |
| 7,720,720 B1 | 5/2010 | Sharma et al. |
| 9,244,989 B2 | 1/2016 | Boross et al. |
| 10,026,045 B1 | 7/2018 | Portnoy et al. |
| 2003/0233032 A1 | 12/2003 | Teicher et al. |
| 2005/0160084 A1 | 7/2005 | Barrett |

(Continued)

*Primary Examiner* — William L Bashore
*Assistant Examiner* — Hwei-Min Lu
(74) *Attorney, Agent, or Firm* — Ference & Associates LLC

(57) ABSTRACT

Systems and methods are provided for displaying graphical objects in a user interface of a mobile device. In one embodiment, methods may include receiving a request to display a primary status associated with a plurality of facilities, querying at least one database for data associated with each one of the plurality of facilities, calculating a score for each one of the plurality of facilities based on the associated data, determining the primary status associated with each one of the plurality of facilities based by comparing the score with threshold rules, selecting a primary graphical object style for each one of the plurality of facilities based on the primary status, and generating for display a user interface screen including primary graphical objects in a screen of the mobile device, wherein the primary graphical objects include the respective selected style.

19 Claims, 19 Drawing Sheets

(56) References Cited

U.S. PATENT DOCUMENTS

| | | | |
|---|---|---|---|
| 2006/0041368 A1* | 2/2006 | Williams | F02C 9/42 701/100 |
| 2006/0276200 A1* | 12/2006 | Radhakrishnan | H04W 4/029 455/456.1 |
| 2007/0233854 A1 | 10/2007 | Bukovec et al. | |
| 2008/0281607 A1 | 11/2008 | Sajja et al. | |
| 2009/0037837 A1 | 2/2009 | Raghunath et al. | |
| 2010/0049473 A1 | 2/2010 | Regnard De Lagny et al. | |
| 2010/0131282 A1* | 5/2010 | Rowe | G06Q 10/06 705/2 |
| 2011/0046498 A1 | 2/2011 | Klap et al. | |
| 2011/0119651 A1* | 5/2011 | Utschig-Utschig | G06F 8/35 717/107 |
| 2011/0131122 A1 | 6/2011 | Griffin et al. | |
| 2012/0221582 A1* | 8/2012 | Boross | G06F 16/26 707/752 |
| 2012/0290323 A1 | 11/2012 | Barsoum et al. | |
| 2013/0139102 A1 | 5/2013 | Miura et al. | |
| 2013/0173281 A1* | 7/2013 | Rosow | G06Q 10/087 705/2 |
| 2014/0074421 A1 | 3/2014 | Yin et al. | |
| 2014/0108033 A1 | 4/2014 | Akbay et al. | |
| 2014/0137024 A1 | 5/2014 | Curtis | |
| 2014/0258940 A1 | 9/2014 | Han et al. | |
| 2015/0020091 A1 | 1/2015 | Roberts et al. | |
| 2015/0142643 A1 | 5/2015 | Ceribelli et al. | |
| 2015/0248214 A1 | 9/2015 | Gilger et al. | |
| 2015/0370993 A1 | 12/2015 | Moturu et al. | |
| 2016/0019352 A1 | 1/2016 | Cohen et al. | |
| 2016/0063205 A1 | 3/2016 | Moturu et al. | |
| 2016/0140091 A1 | 5/2016 | Bhat | |
| 2016/0217404 A1 | 7/2016 | Ross et al. | |
| 2016/0224917 A1 | 8/2016 | Ross et al. | |
| 2016/0292197 A1 | 10/2016 | Morimoto et al. | |
| 2016/0378302 A1* | 12/2016 | Gilger | G06Q 10/067 715/736 |
| 2019/0121685 A1 | 4/2019 | Coutinho et al. | |

* cited by examiner

SYSTEMS AND METHODS FOR GENERATING INTERACTIVE HYPERMEDIA GRAPHICAL USER INTERFACES ON A MOBILE DEVICE

CROSS REFERENCE TO RELATED APPLICATIONS

This application claims priority to co-pending U.S. patent application Ser. No. 15/798,609, filed on Oct. 31, 2017, titled "Systems and Methods for Generating Interactive Hypermedia Graphical User Interfaces on a Mobile Device," which claims priority to U.S. Provisional Application Ser. No. 62/415,127, filed on Oct. 31, 2016, titled "Systems and Methods for Generating Interactive Hypermedia Graphical User Interfaces on a Mobile Device," the contents of both of which are incorporated by reference herein.

BACKGROUND

In recent years, the amount of electronic information available to a user has increased exponentially. Some estimates indicate that a user device, such as smartphone or tablet, has potential access to petabytes of information. The increased availability of information has important advantages and created novel services and systems. However, valuable and beneficial use of information demands improved techniques to search, aggregate, and present data. Techniques that synthesize and filter information before it is presented to a user are necessary to manage large data sets and create useful services. These techniques are particularly important when users utilize mobile devices. Mobile devices normally have a limited screen size and restricted user interaction options. Therefore, methods and systems for clear and efficient presentation of information in mobile devices are of utmost importance. In addition, effective use and presentation of information in mobile devices require efficient communication protocols and methods. Information feeding a user device may come from a plurality of locations and a seamless interaction with the different information sources is increasingly important.

Object-oriented graphical user interfaces (GUIs) are an alternative for displaying and manipulating information. Object-oriented GUIs normally uses a plurality of graphical objects on the screen, such as icons and windows, which may quickly present information to the user. Furthermore, each graphical object may be associated with a different information provider and the GUI compiles information from multiple sources. Even though the use of graphical objects on the screen improves information presentation, the abilities of current user devices are underutilized when graphical objects only present information. Current user devices have access to complementary information through networks quickly providing additional information to the user. Also, current devices can communicate with other devices and give or receive instructions. Therefore, GUI generation methods that exploit these abilities may improve the user experience by providing additional opportunities from mere information display. There is a pressing need to address shortcomings of current object-oriented GUI generation methods and incorporate user interaction mechanisms, such as hypermedia elements or functions that facilitate further queries and/or communications.

In view of the shortcomings of current methods for object-oriented GUI generation, improved systems and methods for generation of GUIs on mobile devices are presented.

BRIEF SUMMARY

Disclosed embodiments provide improvements in object-oriented graphical user interface generation. Disclosed embodiments use forms of graphical object generation based on scores and thresholds that are used to generate and display graphic styles. In the context of this application, the graphic styles are the combined graphical features in an object and include background color, text color, fonts, size, alignment, formatting, and shapes among others. The disclosed embodiments also provide mechanisms for graphical object generation, data compilation, and rendering. In some embodiments, a method is provided for generating and displaying hierarchical graphical objects. The method may include having a processor generating secondary graphical objects with further information when the user interacts with a primary graphical object. In other embodiments, a method is provided to associate graphical objects with hypermedia elements. Associated graphical objects may then be used to open communication channels and modify parameters used to generate the GUI.

Consistent with the disclosed embodiments, a method is provided for generating a hypermedia graphical user interface for a mobile device. The method may include receiving a request to display a primary status associated with a plurality of facilities, querying at least one database for data associated with each one of the plurality of facilities, calculating a score for each one of the plurality of facilities based on the associated data, determining the primary status associated with each one of the plurality of facilities based by comparing the score with threshold rules, selecting a primary graphical object style for each one of the plurality of facilities based on the primary status; and generating for display a user interface screen including primary graphical objects in a screen of the mobile device, wherein the primary graphical objects include the selected style.

Consistent with the disclosed embodiments, a non-transitory computer readable medium is disclosed. The non-transitory computer readable medium may storing instructions which, when executed, cause at least one processor to perform operations for generating a hypermedia graphical user interface for a mobile device. The operations may include receiving a request to display a primary status associated with a plurality of facilities, querying at least one database for data associated with each one of the plurality of facilities, calculating a score for each one of the plurality of facilities based on the associated data, determining the primary status associated with each one of the plurality of facilities based by comparing the score with threshold rules, selecting a primary graphical object style for each one of the plurality of facilities based on the primary status, and generating for display a user interface screen including primary graphical objects in a screen of the mobile device, wherein the primary graphical objects include the selected style Consistent with yet other disclosed embodiments, a different aspect of the present disclosure is directed to a computerized system generating a hypermedia graphical user interface for a mobile device. The computerized system may include at least one processor in communication with a mobile device associated with a user and a storage medium storing instructions that, when executed, configure the at least one processor to: receive a request to display a primary status associated with a plurality of facilities, query at least one database for data associated with each one of the plurality of facilities, calculate a score for each one of the plurality of facilities based on the associated data, determine the primary status associated with each one of the plurality of facilities based by comparing the score with threshold rules, select a primary graphical object style for each one of the plurality of facilities based on the primary status; and generating for display a user interface screen including primary graphical objects in a screen of the mobile device, wherein the primary graphical objects include the selected style.

The foregoing general description and the following detailed description are exemplary and explanatory only and are not restrictive of the claims.

BRIEF DESCRIPTION OF THE SEVERAL VIEWS OF THE DRAWINGS

The accompanying drawings, which are incorporated in and constitute a part of this specification, illustrate several embodiments and, together with the description, serve to explain the disclosed principles. In the drawings.

DETAILED DESCRIPTION

Reference will now be made in detail to exemplary embodiments, examples of which are illustrated in the accompanying drawing and disclosed herein. Wherever convenient, the same reference numbers will be used throughout the drawings to refer to the same or like parts.

Figure 1:
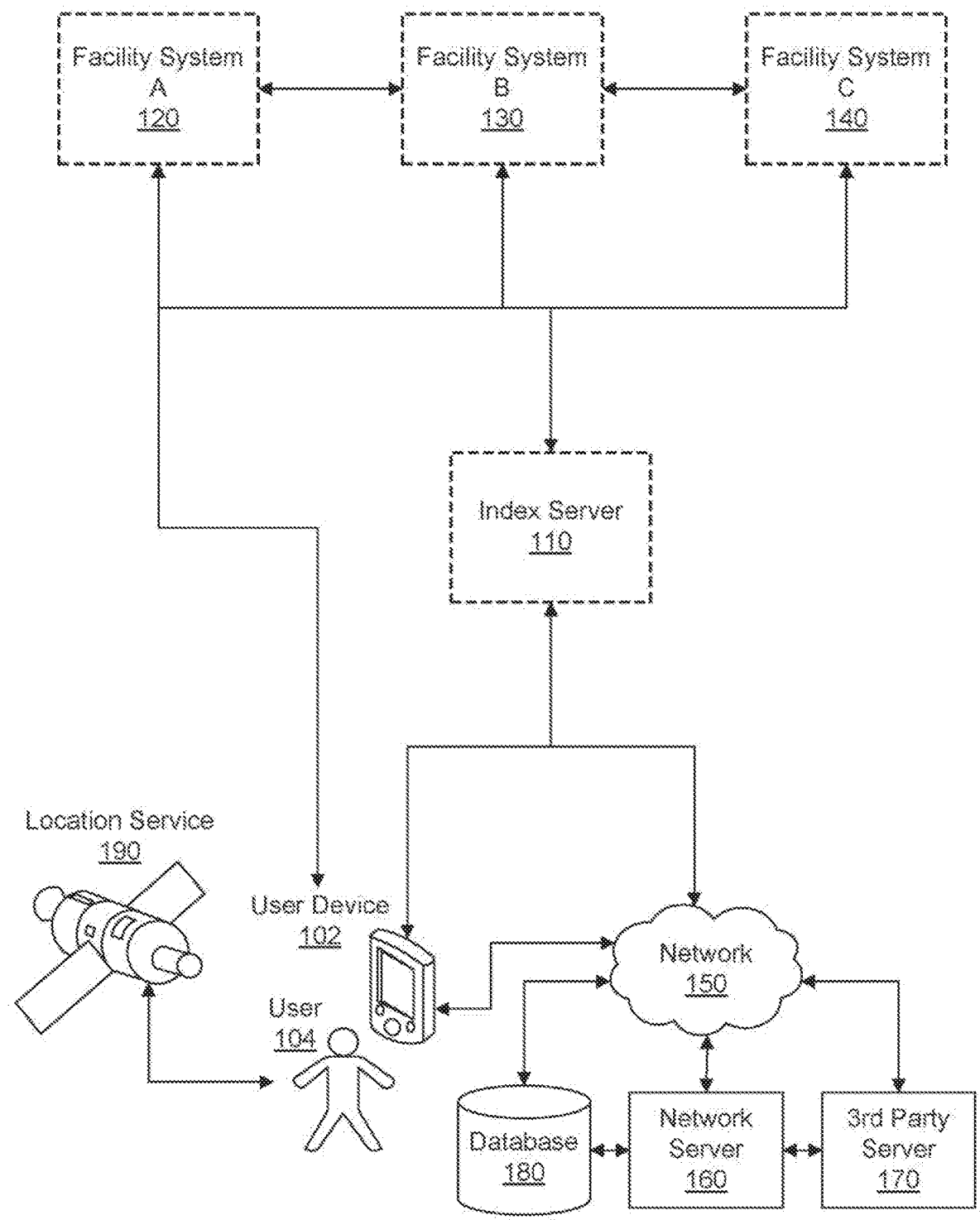
FIG. 1 shows a diagram of a computer system 100 that may be configured to perform one or more software processes that, when executed by one or more processors, perform methods consistent with disclosed embodiments.

FIG. 1 shows a diagram of a computer system 100 that may be configured to perform one or more software processes that, when executed by one or more processors, perform methods consistent with disclosed embodiments. The components and arrangements shown in FIG. 1 are not intended to limit the disclosed embodiments, as the components used to implement the disclosed processes and features may vary.

As shown in FIG. 1, system 100 may include facility system A 120, facility system B 130, and facility system C 140. System 100 may also include interconnected servers. For example, system 100 may include index server 110, network server 160, and 3rd party server 170. Further, system 100 may include external devices like user device 102 (operated by user 104), database 180, and location service 190. The multiple servers and elements of system 100 may communicate with each other directly, through network 150, or through a combination of communications methods.

Facility systems 120, 130, and 140, and index server 110 are displayed as separated entities in FIG. 1. However, they may share components and/or may be the same entity with added components. For example, index server 110 may be part of facility system A 120. Similarly, facility system B 130 and facility system C 140 may share computing machines or may be different departments of a single entity. Additionally, components in system 100 may be virtually or physically defined. For example, database 180 may be different data centers or a virtual data center in network sever 160. Further, 3rd party server 170 and network server 160 may be two independent machines or a single machine with virtual or emulated partitions.

In some embodiments, facilities and index server 110 may connect to user device 102, network 150, network server 160, third party server 170, database 180, and location service 190. These elements may be external to the other facilities, may be contained in a single facility, or may be in a combination of facilities. Other components known in the art may be included in system 100 to perform tasks consistent with the disclosed embodiments.

User device 102 may be a personal computing device such as, for example, a general purpose or notebook computer, a mobile device with computing ability, a tablet, smartphone, wearable device such as Google Glass™ or smart watches, or any combination of these computers and/or affiliated components. In some embodiments, user device 102 may be a computer system or mobile computer device that is operated by user 104. In some embodiments, user device 102 may be associated with a particular individual such as user 104, such that authentication services correlate devices and users.

In some embodiments, user device 102 may communicate with facility systems 120, 130, and 140, and/or index server 110 via direct wireless communication links (not shown), or network 150.

Network 150 may comprise any type of computer networking arrangement used to exchange data. For example, network 150 may be the Internet, a private data network, virtual private network using a public network, and/or other suitable connection(s) that enables system 100 to send and receive information between the components of system 100. Network 150 may also include a public switched telephone network ("PSTN") and/or a wireless cellular network.

Network server 160, third party server 170, and database 180 may be one or more servers or storage services provided by an entity such as a provider of networking, cloud, or backup services. For example, in some embodiments, network server 160 may be associated with a cloud computing service such as Microsoft Azure™ or Amazon Web Services™. In such embodiments, network server 160 may comprise a plurality of geographically distributed computing systems executing software for performing one or more functions of the disclosed methods. Additionally, in some embodiments, third party server 170 may be associated with a messaging service, such as, for example, Apple Push Notification Service, Azure Mobile Services, or Google Cloud Messaging. In such embodiments, third party server 170 may handle the delivery of messages and notifications related to functions of the disclosed embodiments, such as task creation, task assignment, task alerts, and task completion messages and notifications.

In some embodiments, system 100 may include configurations that vary from the example shown in FIG. 1, which illustrates a facility systems 120, 130, and 140 and index server 110 working in concert with a cloud computing system including network server 160, third party server 170, and database 180. As a first variation, system 100 may include only facility system A 120, and thus may exclude cloud computing components such as network server 160, third party server 170, and database 180. In such embodiments, facility system A 120 may handle substantially all operations and functions of the present embodiments. As a second variation, system 100 may exclude external components. For example, location service 190 and database 180, may be excluded from system 100. In such embodiments, a cloud computing system including network server 160 and third party server 170, may include elements to handle location and data storage functions.

Figure 2:
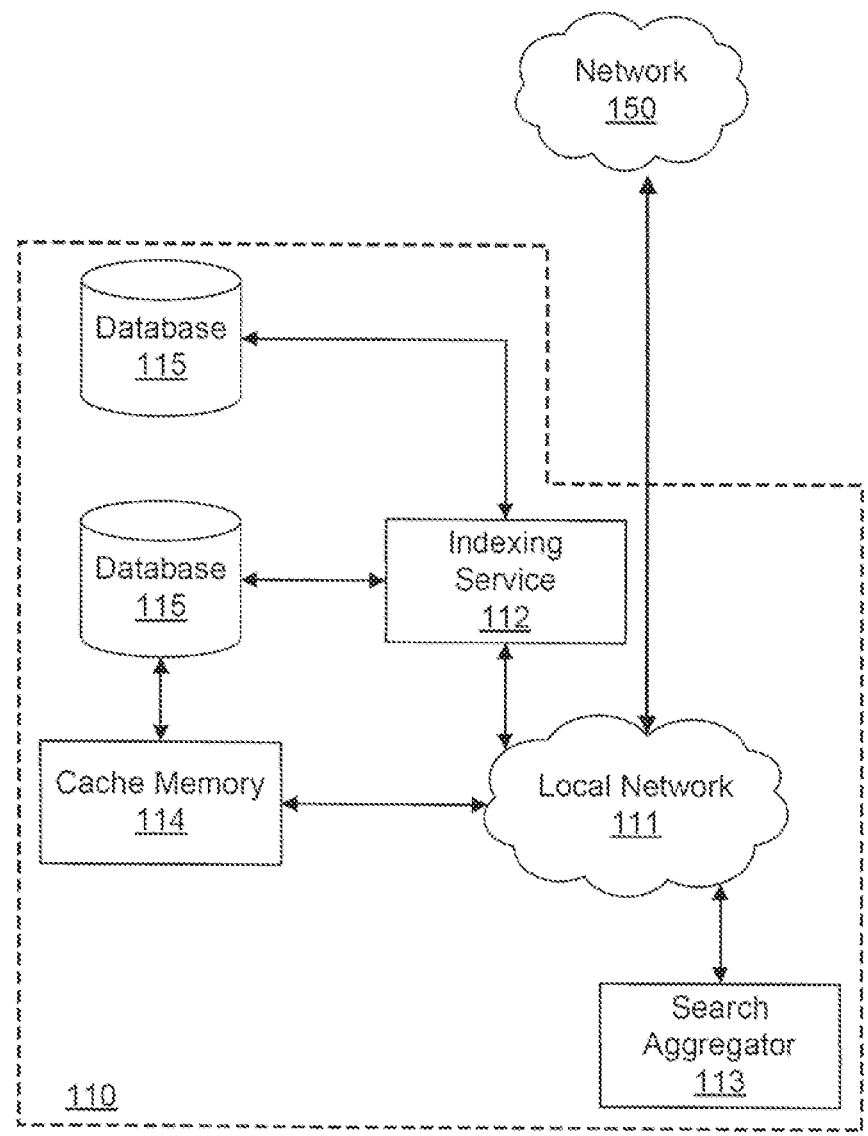
FIG. 2 shows a diagram of an exemplary index server 110, consistent with the disclosed embodiments.

FIG. 2 shows a diagram of an exemplary index server 110, consistent with the disclosed embodiments. Index server 110, may include indexing service 112, local network 111, databases 115, search aggregator 113, and cache memory 114.

Indexing service 112 may be a component configured to provide a plurality of pointers, each pointing, for example, to a storage location associated with certain information. Then, when collecting information, an element in system 100 and connected to network 150 may, for example, look up one or more pointers associated with the desired information type in the index server 110 and may follow the pointer to extract information from one or more databases. In some embodiments, indexing service 112 may dynamically update the various pointers to reflect, for example, changes in storage format and/or location in the relevant databases. In some embodiments, indexing service 112 may additionally store extracted information in cache memory 114 to minimize retrieval times in future requests.

Search aggregator 113 may include a memory device that collects, filters, and groups search results. As elements in system 100 connected to network 150 generate queries to the multiple databases, search aggregator 113 may receive and store the generated results. Once a search process is complete, search aggregator 113 may forward the total results to another device of system 100. For example, search aggregator 113 may provide complete results in a single transmission anytime user device 102 requests information. Search aggregator 113 may apply a format to the documents based on the particular searches or the device from which the query was generated.

Index server 110 may also include cache memory 114. As discussed before cache memory 114 may be hardware with rapid access memory that stores information collected by indexing service 112. Cache memory 114 may store information frequently accessed by user device 102 or facility systems 120, 130, and 140. For example, cache memory may be configured to store information of the overall occupancy of facilities, available rooms, and/or available staff.

Figure 3:
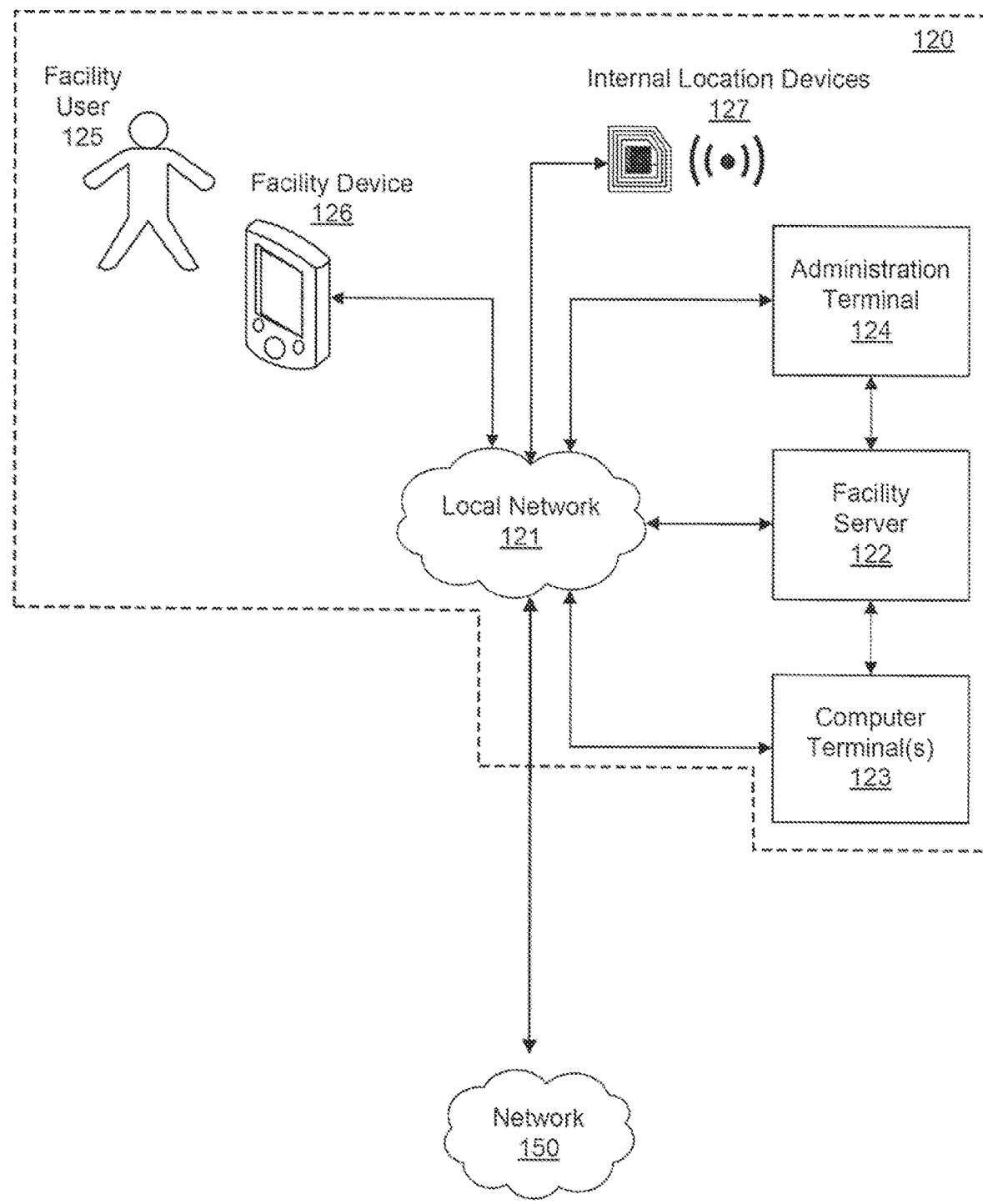
FIG. 3 shows a diagram of an exemplary facility system A 120, according to disclosed embodiments.

FIG. 3 shows a diagram of an exemplary facility system A 120, according to disclosed embodiments. Facility system A 120 may include facility server 122, computer terminal 123, administration terminal 124, facility device 126, facility user 125, and internal location devices 127. Elements in facility system 120 may communicate through local network 121 or directly with each other.

Computer terminal 123 may be a standalone device disposed in an office, a room, an employee station, or an alternative central location in a workplace. In some embodiments, computer terminal 123 may be a desktop or notebook computer, a flat panel or projected display, touch screen monitor, or any other display. In some embodiments, computer terminal 123 may be associated with a particular room in a facility, such as a particular patient room, hotel room, conference room, or any other type of room. Thus, a message or task request received from a computer terminal 123 may automatically associate the task request or message with the room in which computer terminal 123 is installed.

Administration terminal 124 may include a computer system or device associated with a user 104 that manages or oversees a portion of facility system A 120. For example, administration terminal 124 may comprise a computer system located at a head nurse station, a housekeeping manager's office, or any other department manager's office or station.

Facility user 125 may be an individual with a relationship with facility system A 120. For example, facility user 125 may be an employee in a workplace environment such as a physician, nurse, technician, supervisor, manager, support personnel, dispatcher, or any other individual involved with facility system A 120. Facility user 125 may also be a patient or a visitor in facility system A 120. Facility user 125 may operate facility device 126, and/or another computer (not shown) to interact with system 100. System 100 may include multiple types of users such as, for example, patient, patients, caregivers, managers, technicians, task requestors, receptionists, and responders.

In some embodiments, user device 102 may communicate with facility server 122 and/or administration terminal 124 via direct wireless communication links (not shown), or via a combination of one or more of local network 121 and/or network 150.

Facility server 122 may be operated by a facility such as a hospital, business, retail location, and the like. Facility server 122 may also be operated by a contractor and/or a software service provider. Facility server 122 may enable communication within a computer-based system including computer system components such as desktop computers, workstations, tablets, hand held computing devices, memory devices, and/or internal network(s) connecting the components.

Local network 121 may comprise any type of computer networking arrangement used to exchange data in a localized area, such as WiFi, Bluetooth™ Ethernet, and other suitable short-range connections that enable computer terminal 123, facility server 122, administration terminal 124, internal location devices 127, and facility device 126, to send and receive information between the components of facility system 120. In some embodiments, local network 121 may be excluded, and connected elements may communicate with system 100 components via network 150. In some embodiments, connected components may communicate with one or more system 100 components via a direct wired or wireless connection. In some embodiments, local networks 121 may comprise a portion of network 150 or an extension of network 150.

Figure 4:
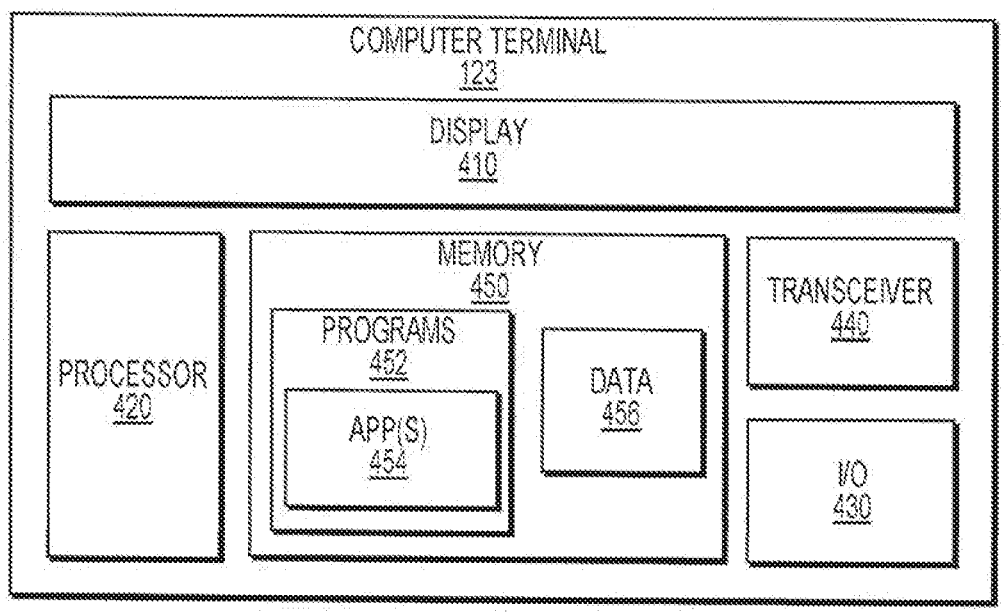
FIG. 4 shows a diagram of computer terminal 123, consistent with disclosed embodiments.

FIG. 4 shows a diagram of computer terminal 123, consistent with disclosed embodiments. As shown, computer terminal 123 may include a display 410, one or more processors 420, input/output ("I/O") devices 430, a transceiver 440, and memory 450.

Display 410 may include one or more screens for displaying task management information such as, for example, liquid crystal display (LCD), plasma, cathode ray tube (CRT), or projected screens.

Processor 420 may be one or more known processing devices, such as microprocessors manufactured by Intel™ or AMD™ or licensed by ARM. Processor 420 may constitute a single core or multiple core processors that executes parallel processes simultaneously. For example, processor 420 may be a single core processor configured with virtual processing technologies. In certain embodiments, processor 420 may use logical processors to simultaneously execute and control multiple processes. Processor 420 may implement virtual machine technologies, or other known technologies to provide the ability to execute, control, run, manipulate, store, etc. multiple software processes, applications, programs, etc. In another embodiment, processor 420 may include a multiple-core processor arrangement (e.g., dual, quad core, etc.) configured to provide parallel processing functionalities to allow computer terminal 123 to execute multiple processes simultaneously. Other types of processor arrangements could be implemented that provide for the capabilities disclosed herein.

I/O devices 430 may include one or more devices that allow computer terminal 123 to receive input from a user. I/O devices 430 may include, for example, one or more pointing devices, keyboards, buttons, switches, touchscreen panels, cameras, barcode scanners, radio frequency identification (RFID) tag reader, and/or microphones.

Transceiver 440 may include one or more communication modules for establishing communication between computer terminal 123 and other devices of system 100 via, for example, local network 121 and/or network 150. For example, transceiver 440 may include circuitry and one or more antennas for communicating wirelessly with local network 121 using a short range/near-field wireless communication protocol such as Bluetooth™, Bluetooth™ LE, WiFi, and Zigbee™. Further, transceiver 440 may communicate with network 150 and/or local network 121 using any known network protocol including any form of wired or wireless internet access.

Memory 450 may include a volatile or non-volatile, magnetic, semiconductor, solid-state, tape, optical, removable, non-removable, or other type of storage device or tangible (i.e., non-transitory) computer-readable medium that stores one or more program(s) 452, such as app(s) 454, and data 456. Data 456 may include, for example, user information, task information, and display settings and preferences. In some embodiments, data 456 may include one or more rule sets for prioritizing and assigning tasks to one or more employees.

Program(s) 452 may include operating systems (not shown) that perform known operating system functions when executed by one or more processors. By way of example, the operating systems may include Microsoft Windows™, Unix™, Linux™ Android™ and Apple™ operating systems, Personal Digital Assistant (PDA) type operating systems, such as Microsoft CE™, or other types of operating systems. Accordingly, disclosed embodiments may operate and function with computer systems running any type of operating system. Computer terminal 123 may also include communication software that, when executed by a processor, provides communications with network 150 and/or local network 121, such as Web browser software, tablet, or smart hand held device networking software, etc.

Program(s) 452 may also include app(s) 454, such as a calendars and workflow management app, which when executed causes computer terminal 123 to perform processes related to creating one or more facilities, managing the created facility census, and tacking emergency room status or housekeeping metrics such as bed turns. For example, app(s) 454 may configure computer terminal 123 to generate and display one or more dynamic calendars and control interfaces, to provide a status of the facility, display a real-time status of the facility capacity, identify potential delays or complications, and provide one or more alternative workflows to mitigate the delays or complications, receive instructions from one or more facility user 125. Furthermore, app(s) 454 may perform one or more automated tasks associated with the facility management, for example, generating order to transfer patients based on the census or housekeeping information, canceling and/or rescheduling one or more job tasks based on changes in the facility status, requesting equipment or supplies associated with a task, and tracking the real-time status of all tasks related. In some embodiments, app(s) 454 may configure one or more computer systems to analyze historical facility performance to identify patterns, trends or correlative relationships in the historical data. For example, trends in historical data may indicate that certain periods experience complications in specific departments. Historical data, identified trends and patterns, and correlative relationships may be identified through regression analysis, queuing analysis and other known statistical analysis methods, stored, and recalled during the creation and/or modification of new patient itineraries, to provide ever-improving patient care and efficiency. Correlations could be stored, retrieved and processed as Stochastic Information Packets (SIPs), Distribution Strings (DIST) or Stochastic Library Unit with Relationships Preserved (SLURPs).

Figure 5:
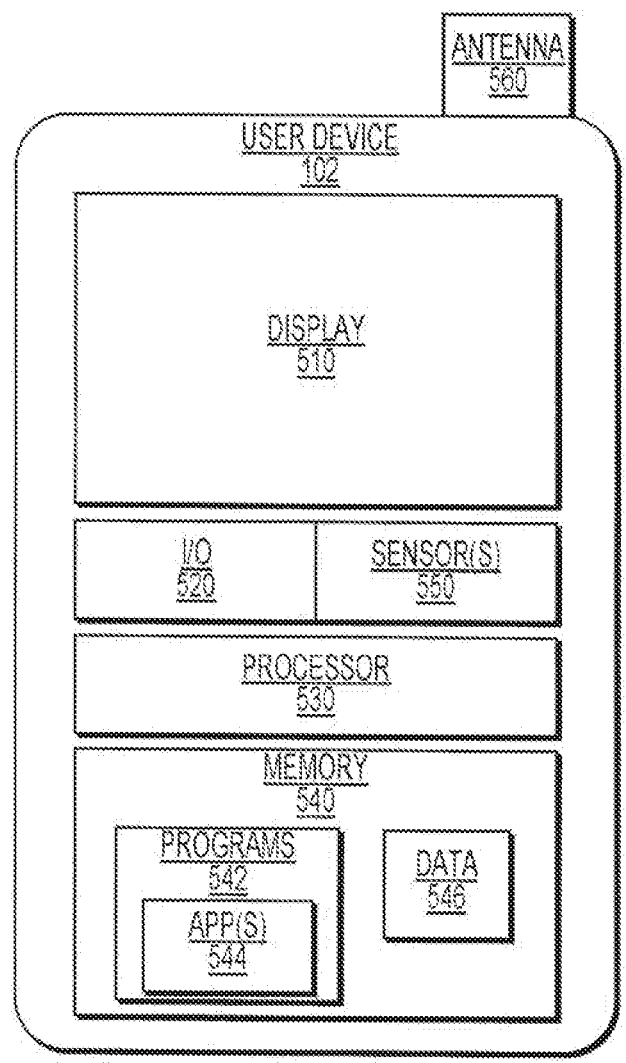
FIG. 5 shows a diagram of an exemplary user device 102, consistent with disclosed embodiments.

FIG. 5 shows a diagram of an exemplary user device 102, consistent with disclosed embodiments. As shown, user device 102 may include display 510, I/O device(s) 520, processor 530, memory 540 having stored thereon data 546 and one or more programs 542, such as app(s) 544, sensor(s) 550, and antenna 560.

Display 510 may include one or more devices for displaying information, including but not limited to, liquid crystal displays (LCD), light emitting diode (LED) screens, organic light emitting diode (OLED) screens, and other known display devices.

I/O devices 520 may include one or more devices that allow user device 102 to send and receive information. I/O devices 520 may include, for example, a pointing device, keyboard, buttons, switches, and/or a touchscreen panel. I/O devices 520 may also include one or more communication modules (not shown) for sending and receiving information via antenna 560 from other components in system 100 by, for example, establishing wired or wireless connectivity between user device 102 to local networks 121, network 150, or by establishing direct wired or wireless connections between user device 102 and other components of system 100. Direct connections may include, for example, Bluetooth™, Bluetooth LE™, WiFi, near field communications (NFC), or other known communication methods which provide a medium for transmitting data between separate devices. In addition, I/O devices 520 may be embedded in other elements of user device 102. For example, I/O devices 520 may be part of display 510 in the form of a touch screen.

Processor(s) 530 may be one or more known computing devices, such as those described with respect to processor 420 in FIG. 2.

Memory 540 may be a volatile or non-volatile, magnetic, semiconductor, tape, optical, removable, non-removable, or other type of storage device or tangible (i.e., non-transitory) computer-readable medium such as those described with respect to memory 450 in FIG. 4.

In some embodiments, user device 102 may contain one or more sensors 550 for collecting environmental, movement, location, and/or security data. Sensors 550 may include: one or more environmental sensors such as, for example, ambient light sensors, microphones, air pressure sensors, temperature sensors, and humidity sensors; motion detectors such as, for example, GPS receivers, location-based data receivers, accelerometers, and gyroscopes; and security sensors such as, for example, fingerprint readers, retina scanners, and other biometric sensors capable of use for security and individual identification. In some embodiments, processor 530 may use data collected by sensors 550 to control or modify functions of program(s) 542.

Figure 6:
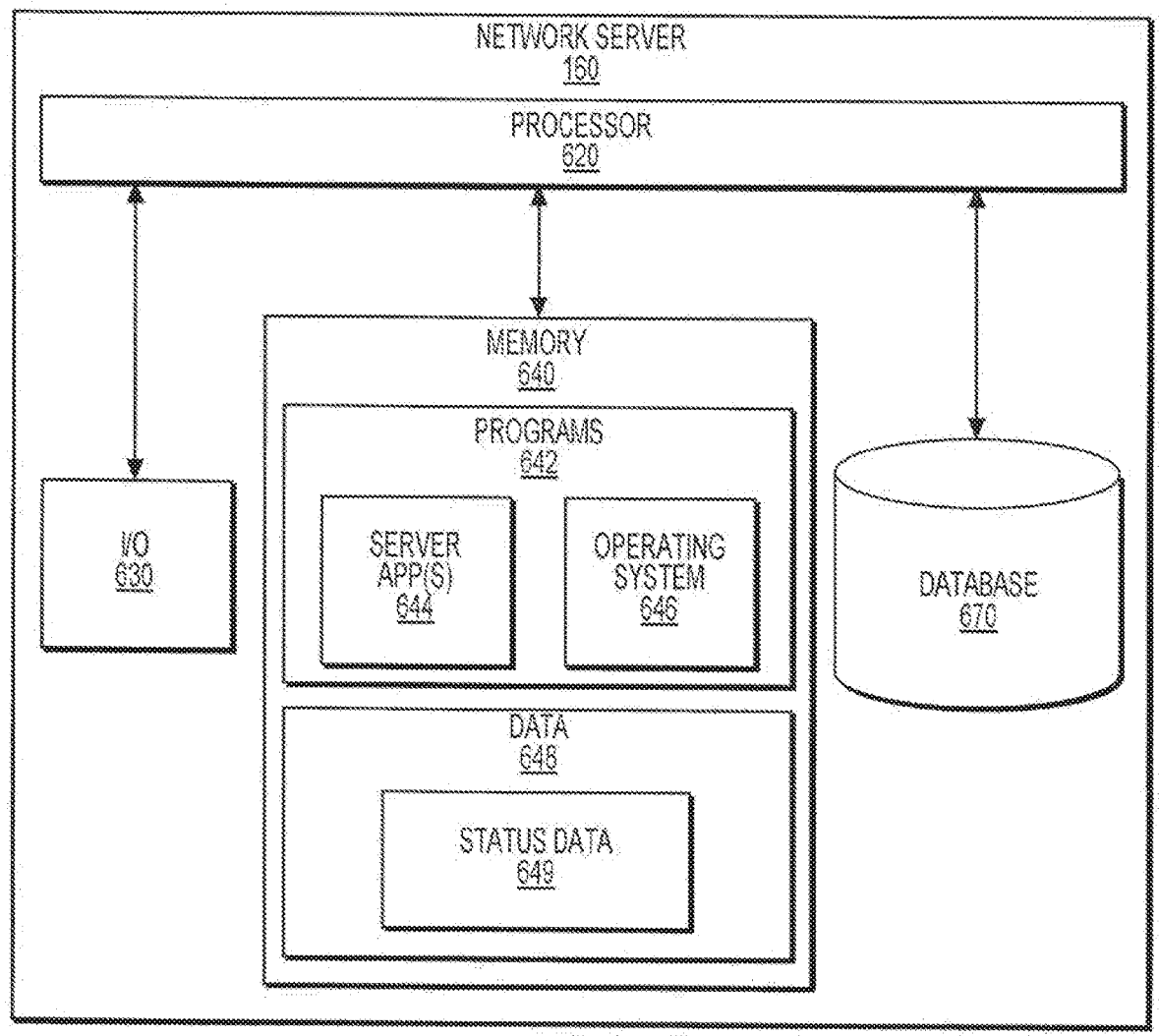
FIG. 6 shows a diagram of an exemplary network server 160, consistent with disclosed embodiments.

FIG. 6 shows a diagram of an exemplary network server 160, consistent with disclosed embodiments. In some embodiments, network server 160 may support or provide a cloud computing service, such as Microsoft Azure™ or Amazon Web Services™. In such embodiments, network server 160 may include one or more distributed computer systems capable of performing distributed computing functions and providing cloud computing services and functions consistent with disclosed embodiments. In some embodiments, network server 160 may operate in conjunction with network server 160. In other embodiments, network server 160 may operate alone, and network server 160 may be replaced by a network connection to network 150 and/or local networks 111 and 121. In such embodiments, network server 160 may perform all functions associated with the disclosed methods. In other embodiments, network server 160 may operate alone, without network server 160. In such embodiments, facility system A 120 may operate as a standalone system, in which network server 160 performs all functions associated with the disclosed methods. Those of ordinary skill in the art will appreciate that the computing arrangements are not limited to these examples, and that other embodiments may include one or more alternate configurations of computing systems capable of performing functions associated with the disclosed embodiments.

As shown in FIG. 6, network server 160 may include one or more processor(s) 620, input/output ("I/O") devices 630, memory 640 storing programs 642 (including, for example, server app(s) 644 and operating system 646) and data 648 (including status data 649), and a database 670. Network server 160 may be a single server or may be configured as a distributed computer system including multiple servers or computers that interoperate to perform one or more of the processes and functionalities associated with the disclosed embodiments.

Processor(s) 620 may be one or more known computing devices, such as those described with respect to processor 420 in FIG. 4.

In some embodiments, network server 160 may also include one or more I/O devices 630 including interfaces for receiving signals or input from devices and providing signals or output to one or more devices that allow data to be received and/or transmitted by network server 160. For example, network server 160 may include interface components, which may provide interfaces to one or more input devices, such as one or more keyboards, mouse devices, and the like, that enable network server 160 to receive input from one or more facility user 125 that is associated with facility system A 120.

In some embodiments, network server 160 may include one or more storage devices configured to store information used by processor 620 (or other components) to perform certain functions related to the disclosed embodiments. In one example, network server 160 may include memory 640 that includes instructions to enable processor 620 to execute one or more applications, such as server applications, an electronic transaction application, an account status application, network communication processes, and any other type of application or software known to be available on computer systems. Alternatively or additionally, the instructions, application programs, etc. may be stored in an internal database 670 or external database 180 (shown in FIG. 1) in communication with network server 160, such as one or more database or memory accessible over network 150. Database 670 or other external storage may be a volatile or non-volatile, magnetic, semiconductor, tape, optical, removable, non-removable, or other type of storage device or tangible (i.e., non-transitory) computer-readable medium.

In one embodiment, network server 160 may include memory 640 which includes instructions that, when executed by processor 620, perform one or more processes consistent with the functionalities disclosed herein. Methods, systems, and articles of manufacture consistent with disclosed embodiments are not limited to separate programs or computers configured to perform dedicated tasks. For example, network server 160 may include memory 640 that may include one or more programs 642 to perform one or more functions of the disclosed embodiments. Moreover, processor 620 may execute one or more programs located remotely from account information display system 100. For example, network server 160 may access one or more remote programs, that, when executed, perform functions related to disclosed embodiments.

Programs 642 stored in memory 640 and executed by processor(s) 620 may include one or more server app(s) 644 and operating system 646. Server app(s) 644 may incorporate one or more apps configured to receive input of information related to tracking facility statuses such as number of patients, average cleaning times, and remission periods, receiving staff schedules and staff skills, receiving one or more hospital rules and legal restrictions, receiving treatment requirements, physicians' orders and regimens associated with patient diagnoses, analyzing received data using one or more rule sets, computer models, or other processing logic, generating data associated with one or more graphical user interfaces, generating one or more communications and/or commands to other computer systems or devices such as user device 102, and updating the graphical user interfaces in real-time based on new data or changes in the analysis results.

In some embodiments, memory 640 may store data 648 including data associated with patients, staff, tasks, assets such as hospital beds, assignment and graphical user interface generation algorithms, historical data, data derived from historical data such as trends, patterns, and correlative relationships. For example, data 648 may include one or more entries including status data 649 (e.g., occupancy of critical care and surgery, schedules, history), medical records, assignment history, conditions, treatment plans, room assignments, room location, and legal and restrictions and regulations. Data 648 may also include information about procedures available in facility system A 120. For the purpose of this application, procedures are not limited to a medical procedure and may include multiple tasks that may be performed within a facility. For example, procedures may refer to medical procedures, such a blood analysis and surgical operations. However, procedures may also refer to doctor appointments, or medical tests, or a scheduled activity. In some embodiments, data 648 is stored in database 670, memory 640, database 180, and any combination thereof.

In some embodiments, memory 640 and database 670 may include one or more memory devices that store data and instructions used to perform one or more features of the disclosed embodiments. Memory 640 and database 670 may also include any combination of one or more databases controlled by memory controller devices (e.g., server(s), etc.) or software, such as document management systems, Microsoft SQL databases, SharePoint databases, Oracle™ databases, Sybase™ databases, or other relational databases.

Network server 160 may communicate with one or more remote memory devices (e.g., third party server 170 and/or database 180) through network 150 or a different network (not shown). The remote memory devices may be configured to store information and may be accessed and/or managed by network server 160. By way of example only, the remote memory devices may be document management systems, Microsoft SQL database, SharePoint databases, Oracle™ databases, Sybase™ databases, or other relational databases. Systems and methods consistent with disclosed embodiments, however, are not limited to separate databases or even to the use of a database.

Figure 7:
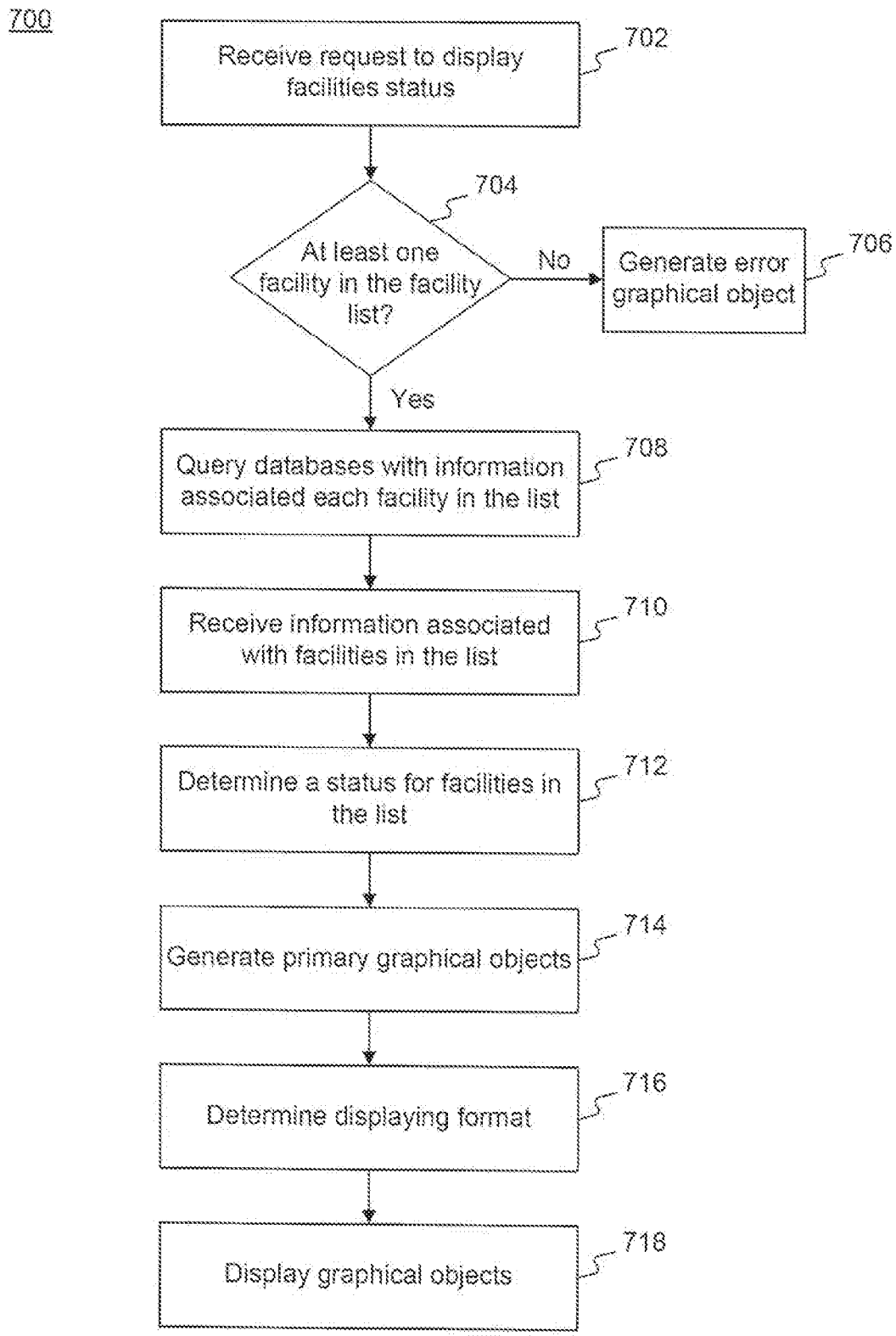
FIG. 7 depicts a flowchart representing an exemplary process 700 for displaying hypermedia graphical objects in a mobile device, consistent with embodiments of the present disclosure.

FIG. 7 depicts a flowchart representing an exemplary process for displaying graphical objects in a mobile device, consistent with embodiments of the present disclosure. In some embodiments, process 700 may be followed by processor 530 that communicates with other elements of system 100 and/or user device 102. Process 700 is described herein as being performed primarily by processor 530. However, in some embodiments process 700 (and other processes disclosed herein) may be performed using one or more other processors and computing systems such as facility server 122, computer terminal 123, network server 160, and any other capable processing systems in communication with network 150.

In step 702, processor 530 may receive a request for information to generate a GUI from other elements of user device 102 such as I/O devices 520, sensor 550, and/or display 510. This request may be a microcontroller instruction, an electrical signal to ports in processor 530, or a query data packet. The request may include information of user 104 such as a name, password, and/or identification number that may be later used for identification purposes.

Processor 530 may continue to step 704 and determine if there is at least one facility in a facility list stored in, for example, memory 540. In some embodiments, the facility list may be a text file with identifiers of a single or a plurality of facilities. In other embodiments, the facility list may be a table or an array in which each position represents a facility. In yet other embodiments, facility list may be an association table with groups of facilities. If processor 530 determines that there is no facility in the facility list (step 704: no), processor 530 may then continue to step 706 and generate an error graphical object that is then displayed in display 510. The error graphical object may include a message that the facility list is empty and colors and icons representative of an empty list or an error in the system. Alternatively, if processor 530 determines that there is at least one facility in the facility list (step 704: Yes), it may continue to step 708.

In step 708, processor 530 may query databases with information associated with each facility in the list. Processor 530 may send independent queries to each facility system via network 150, or it may use index server 110 and send a single query. Also, combination of direct queries with queries through index server 110 may be used. In embodiments, in which the query is sent to index server 110, indexing service 112 may process the query from processor 530 by generating and transmitting independent search queries to each facility system. Additionally, or alternatively, indexing service 112 may query cache memory 114 before sending requests and send request only for missing information. The request from index server 110 may be replied by facility servers in facility systems 120, 130, and 140 with information that may be compiled by search aggregator 113. For example, search aggregator 113 may compile all information in a single file. Search aggregator 113 may also normalize formats and eliminate redundancy.

In step 710, processor 530 may receive information associated with facilities in the list. Information may come from a single source, for example if queries are only directed through index server 110, or may come from a plurality of sources. Processor 530 may then continue to step 712 and process the received information to determine a status for facilities in the facilities list. Processor 530 may make the determination with generation of variables and comparisons as it will be further discussed in process 1000 of FIG. 10. Alternatively, processor 530 may determine the status based on variables transmitted from index server 110 or one of the facility systems. For example, the facility system may include transmit information of its status so processor 530 only replicates the information it receives.

A facility status may be a quantitative or a qualitative value. For example, in some embodiments a facility status may be 'Poor,' 'Fair,' 'Good,' 'Very good,' or 'Excellent. In other embodiments facility status may be numeric and range from '1-5' or '1-10.' In yet other embodiments, the facility status may be color coded to be green, yellow, or red, based on one or more rules sets or lookup tables associating colors with particular numerical status.

In step 714, processor 530 may generate primary graphical objects. It may generate the graphical objects and other components of the GUI following, for example, process 900. Alternatively, it may compose graphical objects using an Application Program Interface (APIs) in programs 542. APIs in user device 102 may include libraries and frame works that map display 510 and communicates with display 510 hardware. For example, APIs in user device 102 may include tools such as SWIG, F2PY, Python interface generator, or Java API.

Processor 530 may also determine a format for displaying generated graphical objects in step 716. In this step processor 530 may query other elements of user device 102, such as programs 542, or memory 540 to determine graphical style for the generated objects. In some embodiments, processor 530 may determine the graphical style as a function of the information received from facilities in the facility list and the determined status. For example, if a facility is determined to be in a poor status processor 530 may determine an emergency graphical style with red colors, bold fonts, and a greater size. However, if a facility is determined to be in a good status, processor 530 may determine to give a calm style with green colors, italic fonts, and standard sizes.

In step 718, processor 530 may display the graphical objects. It may do so by transmitting information to the driver of display 510. In other embodiments, processor 530 may display the graphical objects by directly manipulating RGB tones of pixels in display 510.

As an example of the process described above, a hypermedia graphical user interface may be generated for a hospital system, to effectively convey a high-level real-time status of one or more hospitals within a system or multiple hospitals from different healthcare networks. Processor 530 may continuously query for and receive real-time metric information about a hospital and/or units within the hospital including census information about occupied beds in the hospital, wait times and delays in hospital units, and occupancy rates. Processor 530 may apply one or more rule sets and algorithms to determine statuses of the individual metrics, such as by comparing each metric to a threshold, benchmark, or dynamic range. In some embodiments, processor 530 may determine a score for each metric. Processor 530 may then aggregate the determined scores or statuses, and determine using one or more rule sets or lookup tables whether the aggregate status is within a certain threshold or range. Processor 530 may then generate primary graphical objects reflecting a selected style that corresponds with the determined aggregate status for the hospital. The generated graphical object may include hyperlinked information, to associate the graphical object with the metric(s) underlying the determined status. Processor 530 may then generate for display a graphical user interface having the hypermedia primary graphical objects, to provide a real-time and composite representation of each selected hospital or facility. Thus, the disclosed embodiments may generate a graphical representation of a large amount of information that could not otherwise be understood and evaluated quickly in an interface showing all of the underlying metrics. Moreover, the graphical user may simultaneously display real-time statuses of multiple hospitals or hospital units in different geographic locations.

Figure 8:
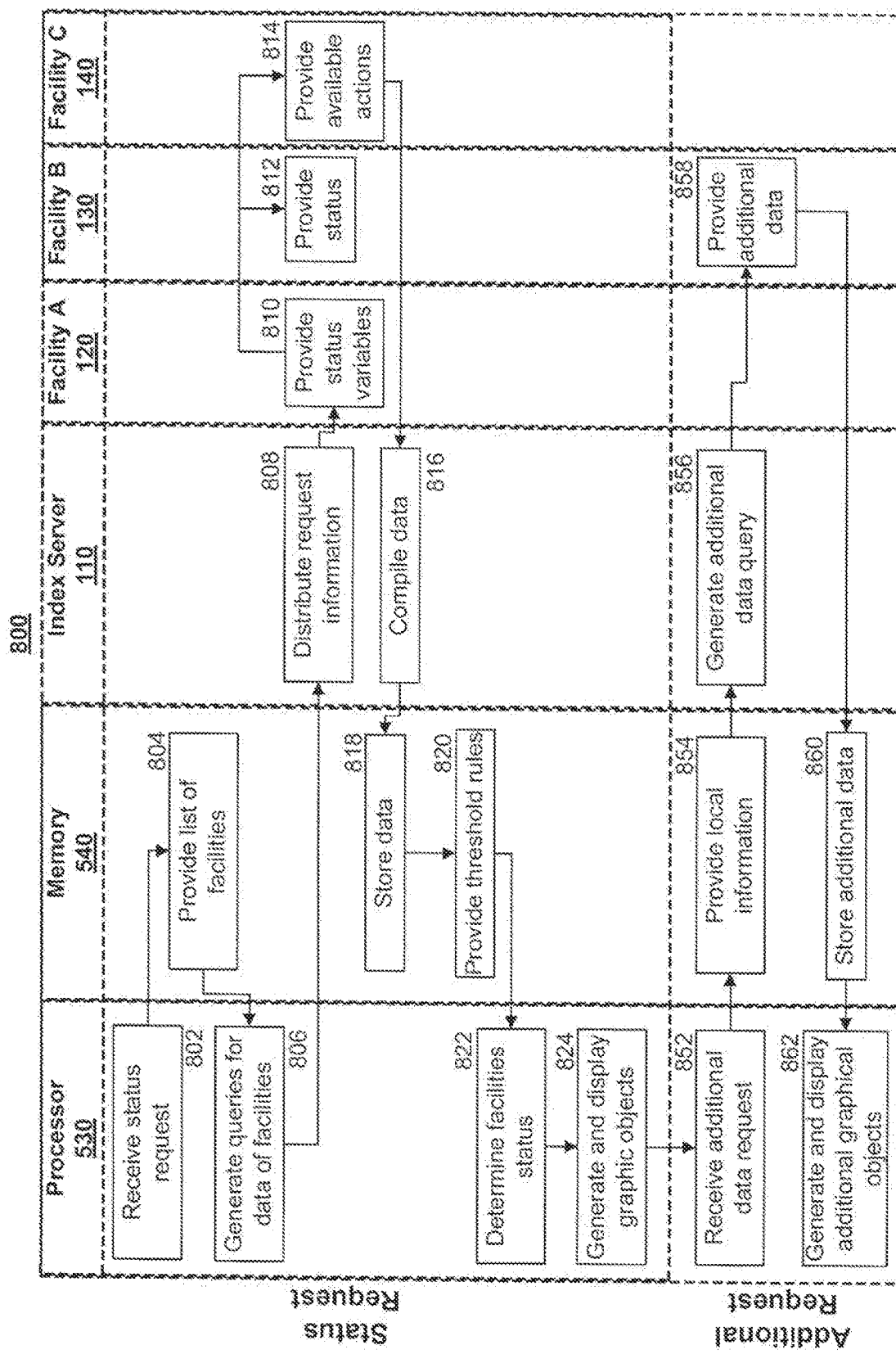
FIG. 8 is a flowchart of an exemplary process 800 for generation and display of requested hypermedia graphical objects, consistent with disclosed embodiments.

FIG. 8 is a flowchart of an exemplary process for generation and display of requested graphical objects, consistent with disclosed embodiments.

Portions of the process 800 are described herein as performed by user device 102 (particularly processor 530, memory 540), index server 110, and facility systems 120, 130, and 140. Further, the process is divided in a "Status Request" and "Additional Request."

Process 800 may begin with a status request from processor 530 to memory 540 in step 802. Processor 530 may initiate routines to generate and display a status GUI, like the one presented in FIG. 13 (described later), when user 104 interacts with user device 102. As a response to the request, in step 804, memory 540 may provide a stored facilities list to processor 530. Additionally, memory 540 may provide stored information of the facilities in the list.

In step 806, processor 530 may determine whether additional information is required to generate and display the GUI. If no more information is necessary to generate the GUI, processor 530 may directly go to step 824 and generate the graphical objects to form the GUI. However, if more information is necessary, processor 530 may generate a single or a plurality of queries for data associated with the facilities in the facilities list.

The queries may be transmitted directly to facility systems 120, 130, and 140, or as presented in FIG. 8, they may go to index server 110. Index server 110 may collect and compile queries and distribute them to the respective facilities in step 808.

Facilities may response to the query from processor 530 or index server 110 by providing status variables (step 810), providing overall status (step 812), and/or providing available actions (step 814). Status variables may include number of patients, number of available beds, longest holding patient, hold hours, average turn time, occupancy of specific departments among others. Overall status, of step 812, may include an already computed status score and include a determined status like the ones described in step 712. The available actions of step 814 may include contact people and/or generate request in facility system by for example interacting with administration terminal 124.

In step 816, index server may compile the information received from the different facilities. For example, index server may summarize all data in a single file. It may also normalize information and transmit the compiled data to user device 102.

In step 818, memory 540 may store the data received from index server 110 or facility systems and then provide it along threshold rules to processor 530 in step 820. Then, step 822 may include processor 530 determining the facilities status with for example processes 1000 described below. Processor 530 may then generate and display primary graphic objects. Primary graphic objects are graphic objects associated with a facility and may include a label and an attribute. The label may identify the facility while the attribute may reflect the associated score. Primary graphic objects may be associated with hypermedia elements to present additional information create new GUIs.

After displaying primary objects, processor 530 may receive additional requests for more information. For example, clicking or dragging of the primary graphical objects may result in a secondary request, or additional request.

The additional request of step 852 may trigger a query to memory 540 to provide additional information locally stored. If all the requested information is in memory 540, step 854 may be immediately followed by step 862, in which processor generate and display secondary or tertiary graphical objects. Secondary and tertiary graphical objects may be similar to primary graphical objects with labels and attributes. However they are restricted to use associated with a subset of the information of a selected primary object. The hierarchical nature of the graphical objects disclosed in this application result in secondary graphical objects including only part of the information of the selected primary graphical object or a subset of the information. In turn tertiary graphical objects are only associated with a subset of a selected secondary object or a subset of information of the selected secondary object.

Processor 530 may generate secondary and tertiary graphical objects based on information stored in memory 540. However, if not all information is available in memory 540, process 800 may continue to step 856 in which additional data queries are generated. The additional queries may be broadcasted to multiple facilities, or as it is presented in FIG. 8, they may be directed to a single facility system (step 858). In some embodiments, facility system may transmit the requested data directly to user device 102. In some embodiments, facility systems 120, 130, and 140 may respond to index server 110, which then compiles information and sends it to user device. In some embodiments, the additional information for secondary or tertiary graphical objects may be stored in memory 540 (step 860), and then transmitted to processor 530. In other embodiments, data for secondary or tertiary graphical objects may be directly transmitted to processor 530. In both situations, in step 862 processor 530 may use the additional data to generate and display secondary and tertiary graphical objects with routines like process 1200 described below.

Figure 9:
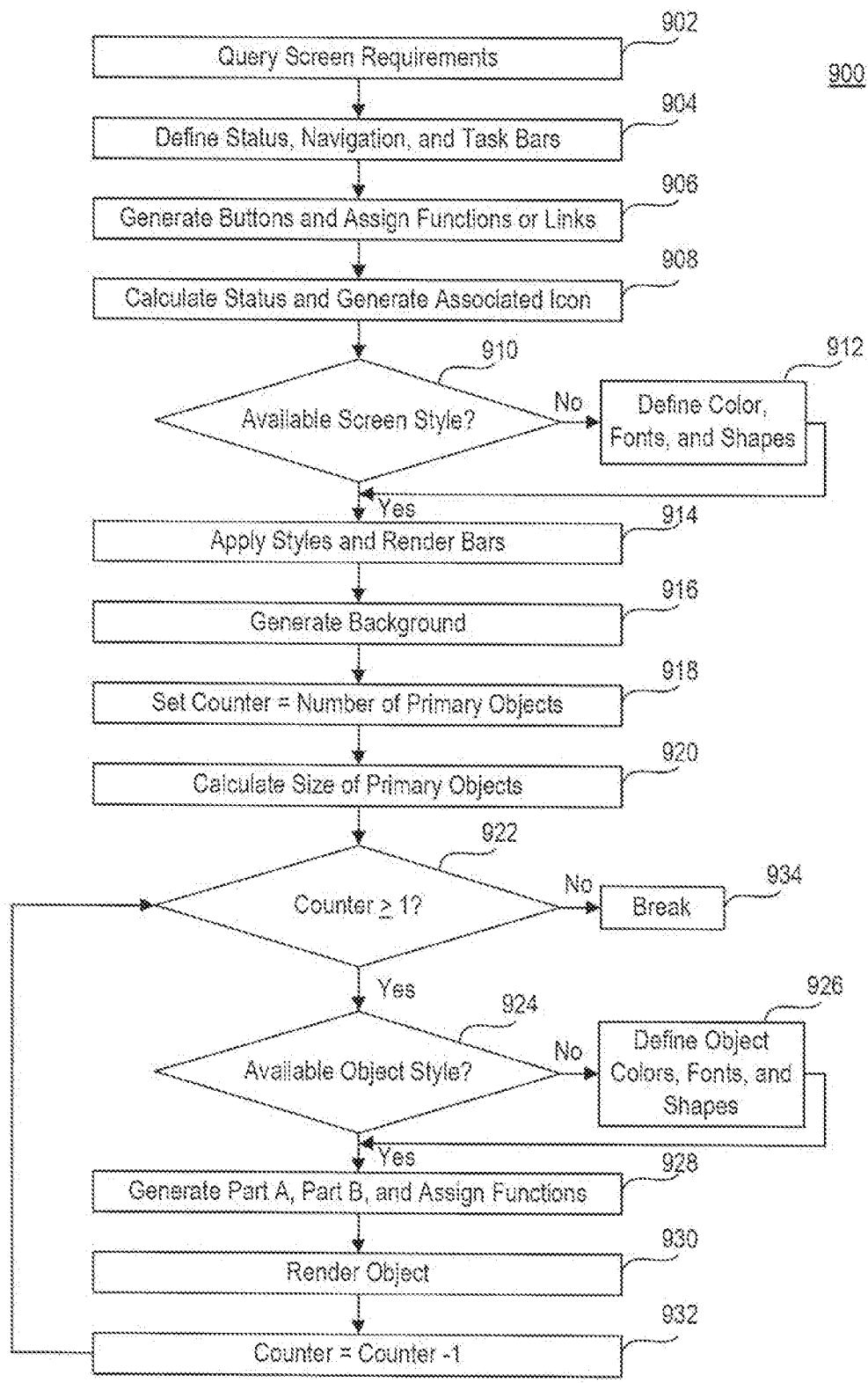
FIG. 9 is a flowchart of an exemplary process 900 for generating and rendering a graphical user interface, according to disclosed embodiments.

FIG. 9 is a flowchart of an exemplary process for rendering a graphical user interface, according to disclosed embodiments. Processor 530 may follow process 900 when generating and display graphical user interfaces with graphical objects. Processor 530 may start by querying screen requirements in step 902.

Processor 530 may then define bars that will be part of the graphical user interface. For example processor 530 may define status bar, navigation bar, and task bar in step 904. In some embodiments, processor 530 may determine sizes, colors and pixels individually for each bar. In other embodiments, processor 530 may select graphic styles for each bar and elements contained inside the bar. Processor 530 may continue to step 906 and generate buttons for the bars. For example, processor 530 may include navigation buttons, task buttons, or menu buttons. In addition, processor 530 may calculate a general status in step 908 to generate an icon or warning elements in the status bar.

In step 910, processor 530 may query other elements of user device 102, such as memory 540 to determine if there are default screen styles available used to render graphical objects in the GUI. In some embodiments, the style for a graphical object may be selected by an application 544 but other embodiments may have user 104 initially determining default styles. If there are hot available styles (step 910: No), processor 530 may continue to step 912 and define the style by determining colors, fonts, shapes, and formatting that will be used to render elements in screen. However, if a style is available (step 910: Yes), processor 530 may continue to step 914 and apply and render the styles to the bars and buttons. In step 916, processor 530 may generate a background. The background may be selected based on the styles selected for bars but may also be defined by the user or the application.

In step 918 processor 530 may prepare to initiate graphical object rendering cycles by setting a counter equal to the number of graphical objects to be displayed. The graphical objects to be displayed may be the facilities in the facilities list (e.g. primary graphical objects), a parameter of the facility (e.g. secondary graphical objects), or a variable of the parameter of the facility (e.g. tertiary graphical objects). As it is described with the former examples, information associated to each tier of graphical object is included within the superior category or is a subset of the superior category. Processor 530 may also calculate the size of the object. It may do so by determining number of current elements on the screen and calculating the available space. It may then divide in the available screen in equal regions to. In some embodiments all elements may have the same shape, but in other embodiments multiple shapes may be used. In addition, some size optimization algorithms maybe used by processor 530 in step 920 to calculate the size of primary objects. For example, iterative algorithms that optimize for greater number of objects in the screen with some restrictions may be used to select the size of the graphical objects.

In step 922, processor 530 may start the iterations and determine if the counter is greater or equal to one. If the counter is not equal or greater to 1 (i.e. there are no facilities in the facility list), it may then continue to step 934 and break the process returning to an idle state or stopping any rending. However, if counter is greater than 1, and graphical objects are ready to be displayed, processor 530 may continue to step 924, in which it determines if there are available styles for objects. Similarly to step 910, in step 924 if there are no styles, processor 530 may define colors, fonts, and shapes for the object at 926. This determination may be based on threshold rules and calculated scores. However, if in step 924 processor 530 determines that there are available object styles, it may continue to step 928.

In some embodiments graphical objects may have multiple parts with distinct styles. For example, a graphical object may include a label and an attribute, which displays information. While the label of the object may have a predefined style, the attribute style may have a dynamic style which is defined as a function of the attribute to be displayed. For instance, an attribute below the threshold, classified as poor, may have a style with a red color, bolded font, and orange background. Similarly, an attribute above the threshold may have a style of green color, italics font, and blue background. Different styles and color may be correlated with the attributes of the graphical object and may reflect determinations of, for example, step 712. Then, in step 928, processor 530 may generate a first (part A) and a second part (part B) of the graphical object. However, some embodiments may have a single part comprising a unique or a plurality of styles. Additionally, some embodiments may have more than two parts. In step 928, processor 530 may also assign functions and hypermedia elements to each part of the graphical object. For example, processor 530 may associate a hypermedia link with the object to open a new GUI. Alternatively, processor 530 may associate parts of the object to functions such as arranging or expanding the objects.

In step 930, processor 530 may render generated objects. It may do so by instructing drivers of display 510 to present the object in a determined position. Step 930 may be similar to step 714 and include communication with display 510 drivers or direct manipulation of pixels in display 510. In some embodiments, processor 530 may render the object using APIs or programs 542 and apps 544 that handle rendering and manipulation of the graphical objects.

In step 932, processor 530 may then reduce the counter and continue the iterations described in step 922. Therefore, in some embodiments, processor 530 will continue generating graphical objects until all of the primary objects are rendered given the equivalence of step 918. Once all graphical objects have been rendered and counter has a value of zero, then in step 922, processor 530 may determine that the counter is no longer grater or equal to 1 and continue to step 934, in which the processor may return to an idle state and wait for instructions.

Figure 10:
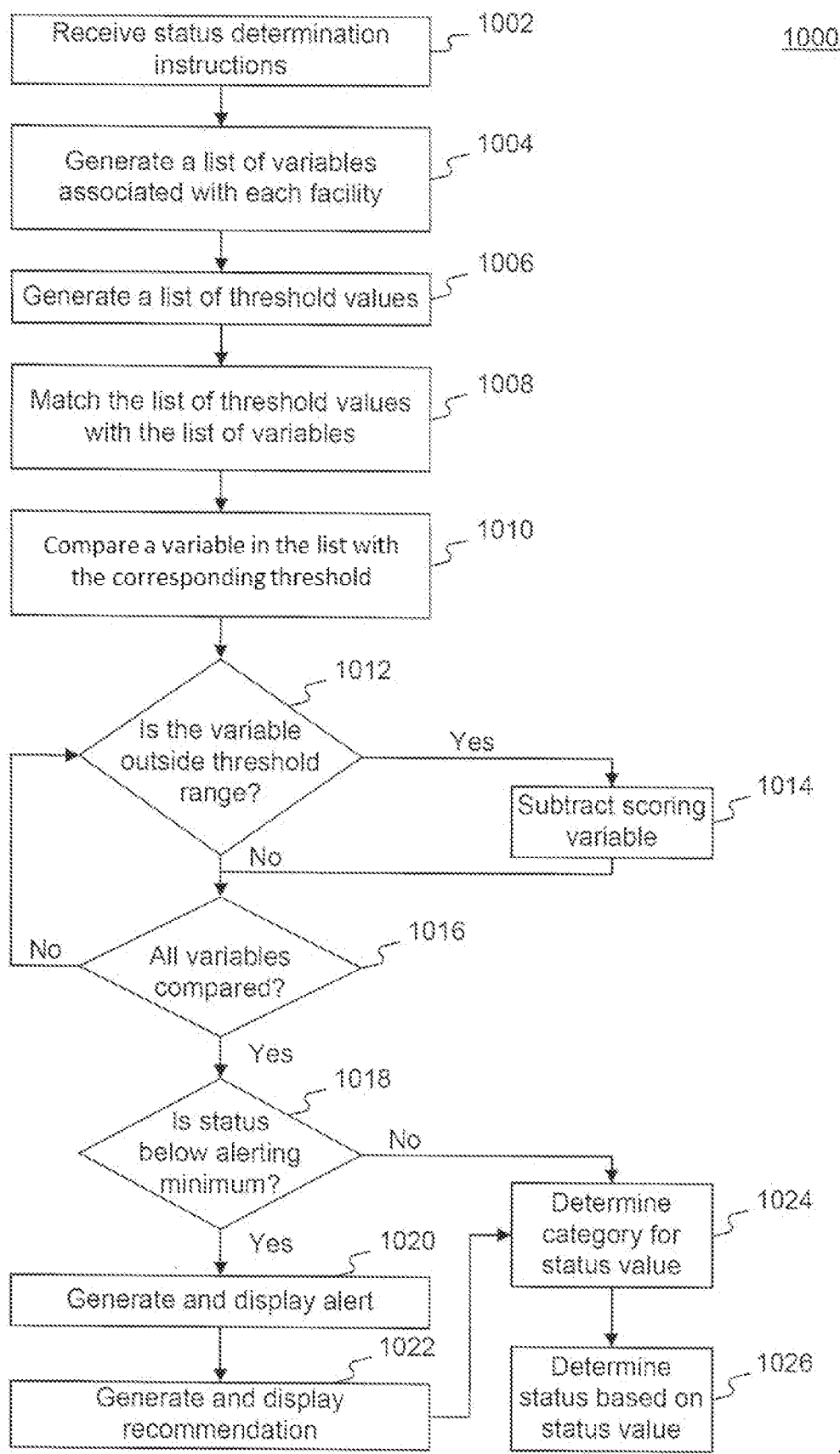
FIG. 10 is a flowchart of an exemplary process 1000 for determining a status, according to disclosed embodiments.

FIG. 10 is a flowchart of an exemplary process for determining a status, according to disclosed embodiments. Processor 530 may follow process 1000 to determine a status associated to facility systems 120, 130, and 140 or one of the variables or parameters within the facilities. The determined status may then be used to generate and display graphical objects with specific graphical styles.

In step 1002, processor 530 may receive instructions to determine a status for facilities in system 100. In some embodiments, instructions may come directly from user 104 or through programs 542 or apps 544. In other embodiments, the status determination may also be requested during process 700 for example in step 712. Then, as a response, processor 530 may generate a list of variables associated with metrics in each facility. Table 1 presents a list of possible metrics received from index server 110 or facility systems 120, 130, and 140 that can be used to generate variables in step 1004 in some embodiments. Variables in table 1 may be Boolean, characters, integers, double, and/or void. In other embodiments, information variables may be generated based on standardized hospital metrics such as The Joint Commission core measures. Variables may be independent of each other or they may be part of a single or a plurality of array and matrixes.

TABLE 1

| Hospital Metrics | |
| --- | --- |
| Average Length of Stay | Market share percentage |
| Time to service | Average daily census |
| Hospital Incidents | Patient throughput volume |
| Patient Satisfaction | Physician satisfaction |
| Physician performance | Average time in ED or ICU |
| Patient readmission rate | Referral volume |
| Inpatient mortality rate | Staff Turnover Rate |
| Operating Margin | Supply Expense per Adjusted Patient |
| Bed Utilization Rate | Medication Error Rate |
| Asset Utilization Rate | Complication Rate |
| Current census | Hospital Acquired Infection Measure |
| Shifts worked per physician | Salary Expense per Adjusted Patient |
| Clinical productivity | Diversion Hours for ED |
| Emergency Department Status | Payor mix |
| Bed Turns | Mortality Rate |
| Bed turn times | Patient length of stay by unit |
| Patient transportation time | Patients boarding in ED |
| Historical census | Patient wait time |
| Return on investment | Gained or lost efficiency |
| Gained or lost margin | Patient wait time |

In step 1006, processor 530 may generate a list of threshold values based on threshold rules stored for example in memory 540. Threshold rules may include series of default values that reflect acceptable values for a specific facility or group of facilities. For example, for some facilities the average length of stay should not be longer than 1 week. Then, in step 1006 processor 530 may generate a list of threshold values, in which the threshold for variable 'Average Length of Stay' is one week. Threshold values may be determined in servers of system 100, such as index server 110, or locally by user 104. In some embodiments, the list of threshold values may be static and have fixed values for comparison. In other embodiments, threshold values may be dynamic and be calculated based on other parameters. For example, instead of having a static 1 week threshold for 'Average Length of Stay,' processor 530 may calculate the threshold using other information as parameters. In some embodiments, processor 530 may take the bed occupancy rate and the patient satisfaction to establish the 'Average Length of Stay' threshold. In such embodiments, if the bed occupancy is low and patient satisfaction is high, processor may determine that the threshold for 'Average Length of Stay' can increase the threshold by adding or multiplying the threshold to 10 days or 2 weeks. In addition, in some embodiments, user 104 may enter threshold estimation and calculation parameters. For example, user 104 may create formulas or equations. Thus, processor 530 may match the list of threshold values with the list of variables.

Processor 530 may then compare each variable in the corresponding threshold and make determinations at step 1010. In some embodiments the comparison may be qualitative and determine only if the variable is below or above the threshold. In other embodiments, the comparison may be quantitative and compare the variable and threshold by classifying in ranges or computing the difference between variables and ranges. In addition, comparing values may include multiplying each value for a scalar. The scalar may be associated with other characteristics of the facility or the other variables. For example, large hospitals may get compared with the threshold value after the threshold is multiplied with a number greater than 1. Then, if processor 530 is determining the status of a large hospital by comparing the number of patients in the intensive care unit (ICU) it will expect to have a greater number of patients than a smaller hospital. This process may be done for each individual variable or for groups of variables in a plurality of combinations or operations.

As a result of step 1010, in step 1012 processor 530 may determine if the variables in the list are outside the threshold range. If processor 530 determines that the variable is not within the threshold, it means the hospital metrics are underperforming and it may proceed to step 1014 in which it may perform an operation to a scoring variable. The scoring variable may be a memory sector in memory 540 that can be manipulated by processor 530. For example, in step 1014, processor 530 may subtract from the scoring variable or may divide the scoring variable by a predetermined number. In some embodiments, changes to the scoring variable by processor 530 may be proportional to a quantitative difference between the variable and threshold. For example, processor 530 may subtract the difference of threshold and variable from the scoring variable. However, if processor 530 determines that the variable is within the threshold range, it may continue to step 1016.

In step 1016 processor 530 may determine if all variables in the list have been compared. When all variables are compared it means that all data from facility systems 120, 130, and 140 has been processed and the processor 530 may continue to step 1018. However, if not all the variables have been compared (step 1016: No). Then, processor 520 may return to step 1012 and continue comparing variables in the list against their corresponding threshold.

If processor 530 continues to step 1018, it may determine if the scoring variable is in an alerting range. An alerting range may be a range of values that indicate one or multiple variables are not within the threshold range. For example, if the scoring variable is below zero it may mean that multiple variables in the list were above the threshold. Then, processor 530 may determine that the score is below a minimum and continue to step 1020 in which it generates and display a graphical object with an alert message based on the score. The graphical object with an alert message may include a predetermined alert graphic style or may include colors and backgrounds of an alert. In addition, in step 1022 processor 530 may also generate recommendations associated with the score or alerting system. For example, if the score is in the alerting range and one of the variables outside the threshold range is 'Bed Turns,' processor 530 may display a recommendation to call more employees. In other embodiments, if the scoring variable is in an alerting range, a sound alert may be generated by processor 530 and be communicated to user 104 with the I/O devices 520.

After step 1022, or if in step 1018 processor 520 determines that the status is not below the minimum (step 1018: No), processor 530 may continue to step 1024 and determine a category for the calculated score. The category may indicate overload and then in step 1026 processor 530 may determine the status of the facility based on scoring variable and/or the number of variables within threshold.

Figure 11:
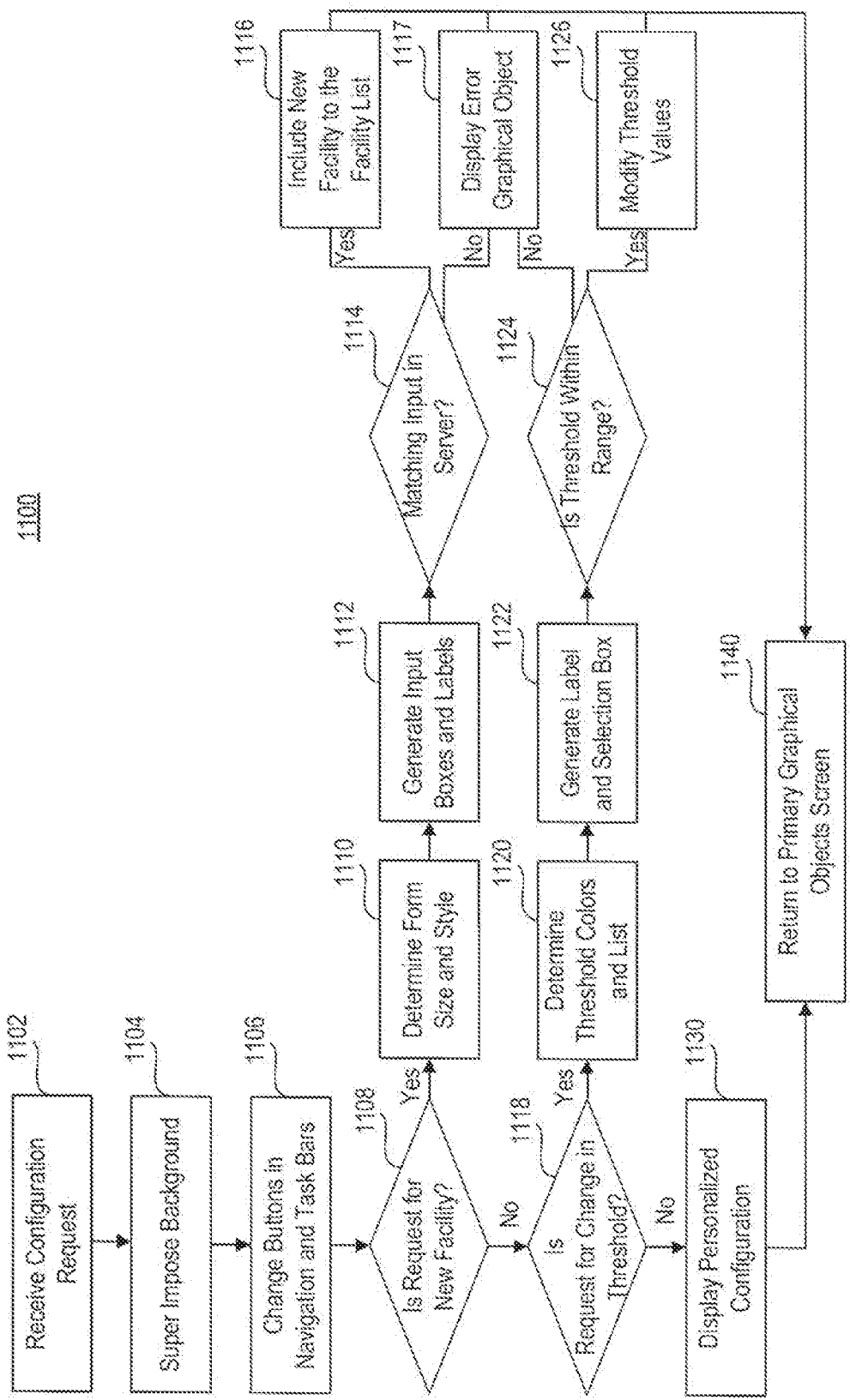
FIG. 11 is a flowchart representing an exemplary process 1100 to display a graphical user interface upon a configuration request.

FIG. 11 is a flowchart representing an exemplary process to display a graphical user interface upon a configuration request. Process 1100 may be conducted by processor 530 when receiving a request for configuration. The request may come from user 104 via I/O devices 520 or may come from other computers of facility systems 120, 130, and 140 or index server 110.

In step 1102, processor 530 may receive the configuration request. For example, user 104 may interact with buttons in the task bar generated in step 906. However, in other embodiments the configuration request may come from computer terminal 123 or one of the servers in system 100.

In step 1104 processor 530 may super impose a background in the GUI of display 510 covering current elements displayed in the GUI. In some embodiments, the background may be superimposed over the entirety of display 510. However, in other embodiments the superimposed background may cover body of GUI, leaving status, navigation, and task bars unmodified. Additionally, processor 530 may change buttons in navigation and task bars in step 1106. For example, processor 530 may include a new button to go back to the previous GUI. In addition, processor 530 may eliminate buttons, such as the arrange button, in step 1106.

In step 1108, processor 530 may determine if the received request is for a new facility. In the event the request is for a new facility (step 1108: Yes), processor 530 may continue to step 1110 and determine size and style for an input form exemplified in FIG. 17 which is further described below. In step 1112, processor 530 may determine the size of input graphical objects, the graphic style of labels and boxes, and then generate and display graphical objects with input boxes and labels. User 104 may then input values in the boxes and processor 530 may continue to step 1114 and contact a server of system 100 to determine if inputted facility matches one of the facilities of system 100. For example, in step 1114 processor 530 may query facilities connected to index server 110. If processor 530 determines that the inputted facility is part of system 100, processor 530 may continue to step 1116 and include the new facility to the facility list. However, if processor 530 determines that the inputted facility does not corresponded to any facility of system 100, it may continue to step 1117 and generate a display a graphical object with an error message.

In the event that processor 530 determines that the request is not for a new facility (step 1108: No), processor 530 may continue to step 1118 and determine if the request is for a change in threshold. When processor 530 determines that the request is for a change in threshold, it may continue to step 1120 and identify a style associated with the threshold graphical objects. For example, processor 530 may select a style for the label of graphical objects that can be modified while having a different style for graphical objects associated with threshold that cannot be modified. In step 1122 may display generate and render label and selection boxes. In some embodiments, the selection objects include a plurality of graphical objects with different styles and associated with specific hypermedia elements. In other embodiments, the selection objects may be dials, input boxes, sliding bars, or a combination of objects. In addition, in some embodiments a single label may be associated with a plurality of selection boxes.

User 104 may then select a threshold or a plurality of thresholds in the GUI and processor 530 may continue to step 1124, in which it determines if the selected threshold is within an acceptable range. Processor 530 may make this determination by locally querying memory 540. However, in other embodiments, processor 530 may send queries to servers of system 100 to determine if the inputted threshold is in an acceptable range. If processor 530 determines that the inputted threshold is within an acceptable range, it may continue to step 1126 and modify threshold values and threshold rules. However, if the selected threshold is not within the range, it may also generate a graphical object with an error message.

If in step 1118, processor 530 determines that the request is not for a change in threshold (step 1118: No), it may continue to step 1130 and display a personalized configuration GUI. The personalized configuration of the GUI may display options on graphical styles, connectivity permissions, account information, or notification controls.

Processor 530 may continue to step 1140 once steps 1116, 1117, 1126, or 1130 are finalized. In step 1140, processor 530 may once again superimpose the background, reverse changes to buttons, and generate primary objects following, for example, process 900.

Figure 12:
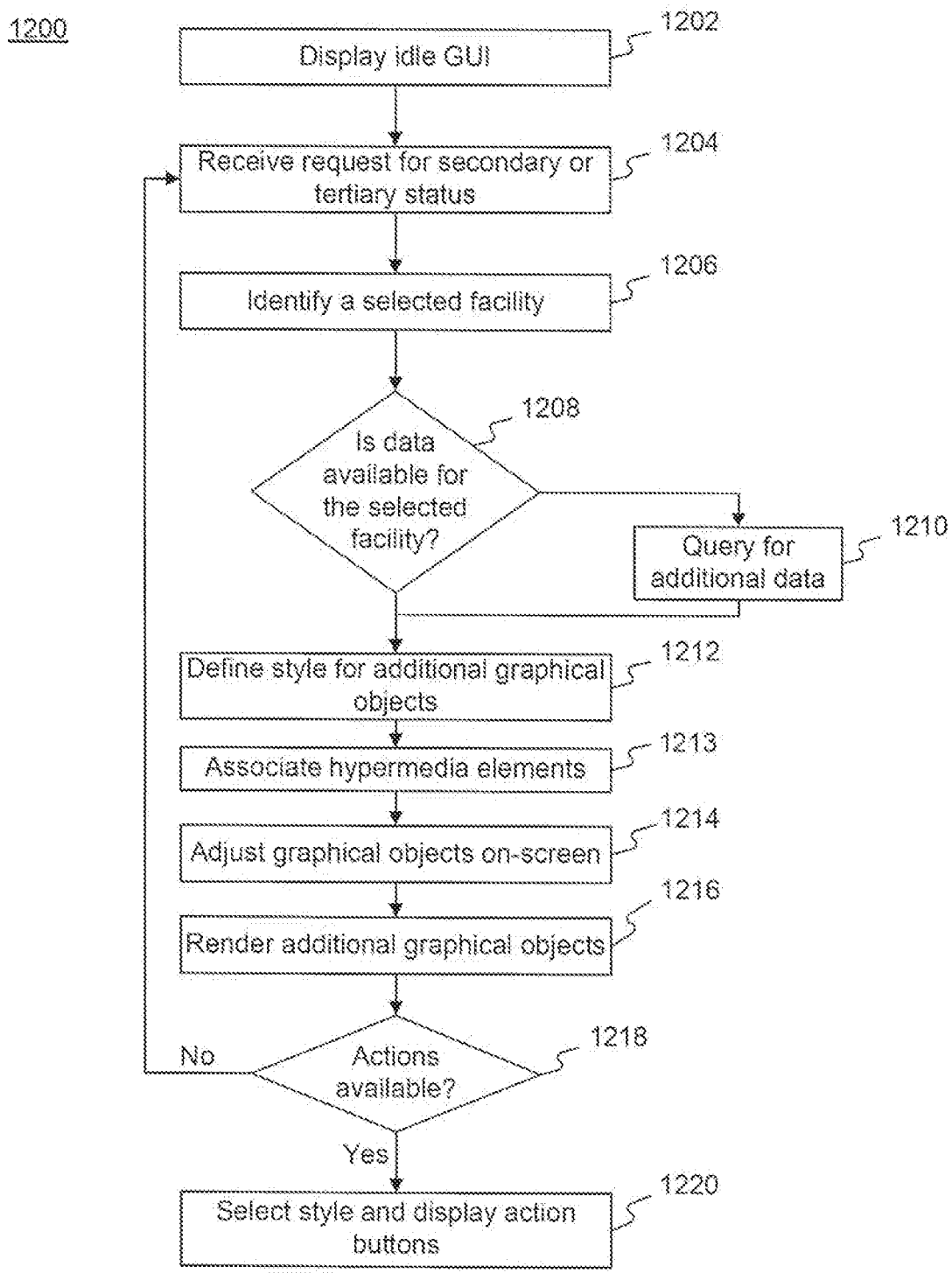
FIG. 12 is a flowchart of an exemplary process 1200 for displaying graphical objects associated with an additional status, according to disclosed embodiments.

FIG. 12 is a flowchart of an exemplary process for displaying graphical objects associated with an additional status, according to disclosed embodiments. Processor 530 may conduct process 1200 to generate and display graphical objects of lower hierarchy than the ones displayed on screen. In some embodiments, lower hierarchy graphical objects, such as secondary and tertiary objects, display subsets of information of higher hierarchy graphical objects. For example, if a primary object represents a hospital, a secondary object may represent a hospital department, and a tertiary object may include a metric for the department. In other embodiments, lower hierarchy elements may include additional information associated with a higher element or display other specific variables.

Process 1200 may start with step 1202 in which the processor display an idle GUI after completing a primary object rendering. In some embodiments, the idle GUI may simply replicate the primary rendering but have processor 530 manipulate display 510 to minimize energy consumption. However, in other embodiments, the idle GUI may include a screensaver or a summary of elements in the primary GUI. For example, the idle GUI may only include warnings and recommendations and turn dark the rest of the screen.

Processor 530 may receive a request for secondary or tertiary status in step 1204. Similarly to steps 702 and/or 1102, processor 530 may receive the request with I/O devices 520, through display 510, or servers of system 100. As a response to the request, processor 530 may identify an object associated with the request and then associate it with a facility system. For example, user 104 may select a graphical object associated with the facility system A by clicking on the primary graphical object associated with facility system A. Then in step 1206, processor 530 may identify facility system A as the facility to be queried.

In step 1208, processor 530 may determine if information for secondary or tertiary objects is locally stored in memory 540. Processor 530 may review the prior records and the variables used to determine the status of the primary object. If processor 530 determines that there is no local information for the selected facility, it may continue to step 1210, in which it may query servers in system 100 for additional information. For example, processor 530 may query index server 110 for additional information when there is no enough information in memory 540. Alternatively, processor 530 may query the identified facility directly for more information.

In step 1212, processor 530 may identify a style for each one of the parts of the additional graphical objects. As in step 928, processor 530 may select styles for the labels, boxes, and attributes of the graphical objects. The selection of styles may be accompanied by the association of hypermedia elements with the graphical objects at 1213. For example, graphical objects may be associated with functions and links that would display other GUIs when selected.

In step 1214, processor 530 may adjust the graphical style, size, and content of graphical objects in the screen. Because process 1200 displays additional graphical objects in the screen, processor 530 modifies graphical objects to open space for new elements. Modifications may include, for example, transparency, color, or size changes. Step 1216 then may have processor 530 rendering the secondary and tertiary graphical objects on the GUI and position them in the available space created by modifying the previous elements.

Step 1218 may have processor determining if there are available actions associated with the newly displayed graphical objects. Available actions may include calling a contact or changing instructions in administration terminal 124. If it determines there are no available actions, processor 530 may return to the idle GUI of step 1202. However, if actions are available (step 1218: Yes), processor 530 may continue to step 1220 and generate and display action buttons associated with the graphical objects. In some embodiments, available actions are display as new parts of the secondary and tertiary graphical objects. In other embodiments, processor may generate additional graphical objects with hypermedia elements associated to the available actions that are then displayed in the vicinity of the new graphical objects. These buttons may include arrows, message bubbles, or other icons associated with activities.

Figure 13:
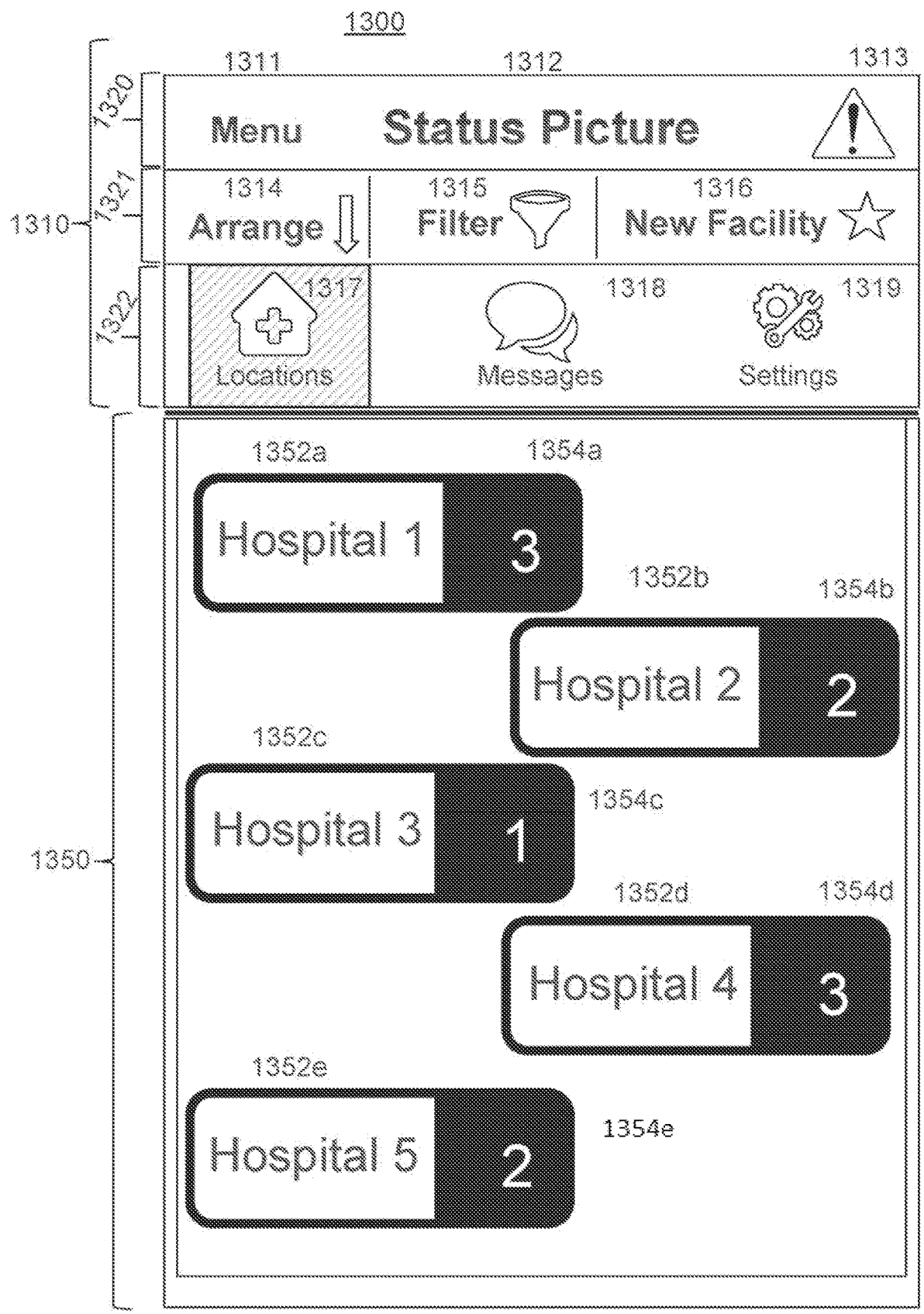
FIG. 13 is an illustration of an exemplary graphical user interface 1300 with primary graphical objects, consistent with the disclosed embodiments.

FIG. 13 is an illustration of an exemplary graphical user interface with primary graphical objects, consistent with the disclosed embodiments. User device 102 may display interface 1300 after processor 530 generates and renders graphical objects based on information of facilities in system 100 and using routines such as process 700. Interface 1300 may be, for example, display in step 718, 824, and/or step 934. After user 104 inputs requests for status information, processor 530 may generate graphical objects associated with hypermedia elements required to display interface 1300.

Interface 1300 may include header section 1310 and body section 1350. Header section 1310 may include a plurality of bars with different functions. In some embodiments, header section 1310 may include status bar 1320, task bar 1321, and navigation bar 1322. Status bar 1320 may include menu icon 1311, status massage 1312, and status icon 1313. Menu icon 1311 may be associated with hypermedia elements to generate additional GUIs or graphical objects and may be associated with hyperlink functions of user device 102 operative system. Status message 1312 may be a text box with information associated with the status of facilities. However, in other embodiments status message 1312 may be a title for interface 1300. Status icon 1313 may be a graphical object displaying an icon associated to the facility. For example, if the status of the facility requires attention, status icon 1313 may include information of the facility. In addition, a plurality of icons may be displayed in status icon 1313 or sub icons, such as numbers or symbols, may also be displayed in status icon 1313.

Task bar 1321 may include a plurality of buttons, including arrange button 1314, filter button 1315, and new facility button 1316. As it is presented in FIG. 13, in some embodiments buttons may include an icon and a label. However, some embodiments may only have one of a label or an icon and yet other embodiments may have multiple labels and icons. Arrange button 1314 may be associated with hypermedia elements to sort objects in body section 1350. Filter button 1315 may instruct processor 530 to generate additional GUIs that present options to filter graphical objects in body section 1350. For example, processor 530 may open GUIs that allow user 104 to select a display with only graphical objects with critical attributes or filters based on the labels. New facility button 1316 may instruct processor 530 to generate new GUIs to enter information about a different facility or include new elements in the facilities list. Other buttons in the task bar such as search buttons, group selection button, or activity buttons may also be displayed in task bar 1321.

Navigation bar 1322 may include buttons that display other interfaces. Similarly to buttons in task bar 1321, buttons in navigation bar may include and icon and/or a label. Additionally, buttons in the navigation bar may change style when they are selected. In the exemplary interface of FIG. 13, locations button 1317 is selected and therefore has a different graphical style. Navigation bar 1322 may include locations button 1317, messages button 1318, and setting button 1319. Selection of navigation buttons may change the body section of interface 1300. For example, locations button 1317 may display the primary objects associated with facilities as it is described in FIG. 13. However, messages button 1318 may change body section and display a messaging board including contacts, prior messages, and an input box. In addition, settings button 1319 may change body section 1350 and present input boxes and labels to change setting of interface 1300 or the processes that are conducted by processor 530 to generate and display graphical objects in the GUI. Although, FIG. 13 presents status bar 1320, task bar 1321, and navigation bar 1322, together in the top of interface 1300 other arrangements are also conceived. For example, navigation bar 1322 may be in the bottom of interface 1300, or task bar 1321 may be on the side of interface 1300. Alternative positions for each one of the bars, and sectioned or divided bars may also be included in interface 1300.

Interface 1300 may also include body section 1350, in which one or a plurality of primary objects may be displayed. As shown in FIG. 13, the primary objects may have a plurality of sections. For example, primary objects may include label section 1352 and attribute section 1354. Label section 1352 may have a plurality of styles may include identification information of a facility. Attribute section 1354 may display an icon or symbol associated with the status of the facility associated to the primary graphical object and determined based on the scoring value. For example, attribute section 1354 may include a number from 1-3 representative of the status of the facility. In other embodiments, attribute section 1354 may display an icon such as a cross, a check mark, or a circle representative of the status of the facility associated with the graphical objects. Yet additional or alternative embodiments may use color codes to represent the associated status or may use ranking system, like 1-5 stars, to represent the status of the facility. In some embodiments, the graphical user interface may include combinations of representations, such as color-coded numbers combined with color coded icons. In addition, one or more of the edges of primary objects in body section 1350 may be color coded or have some other representation of the associated status. For example, one or more edges of the object may have a color associated with the determined status.

Figure 14:
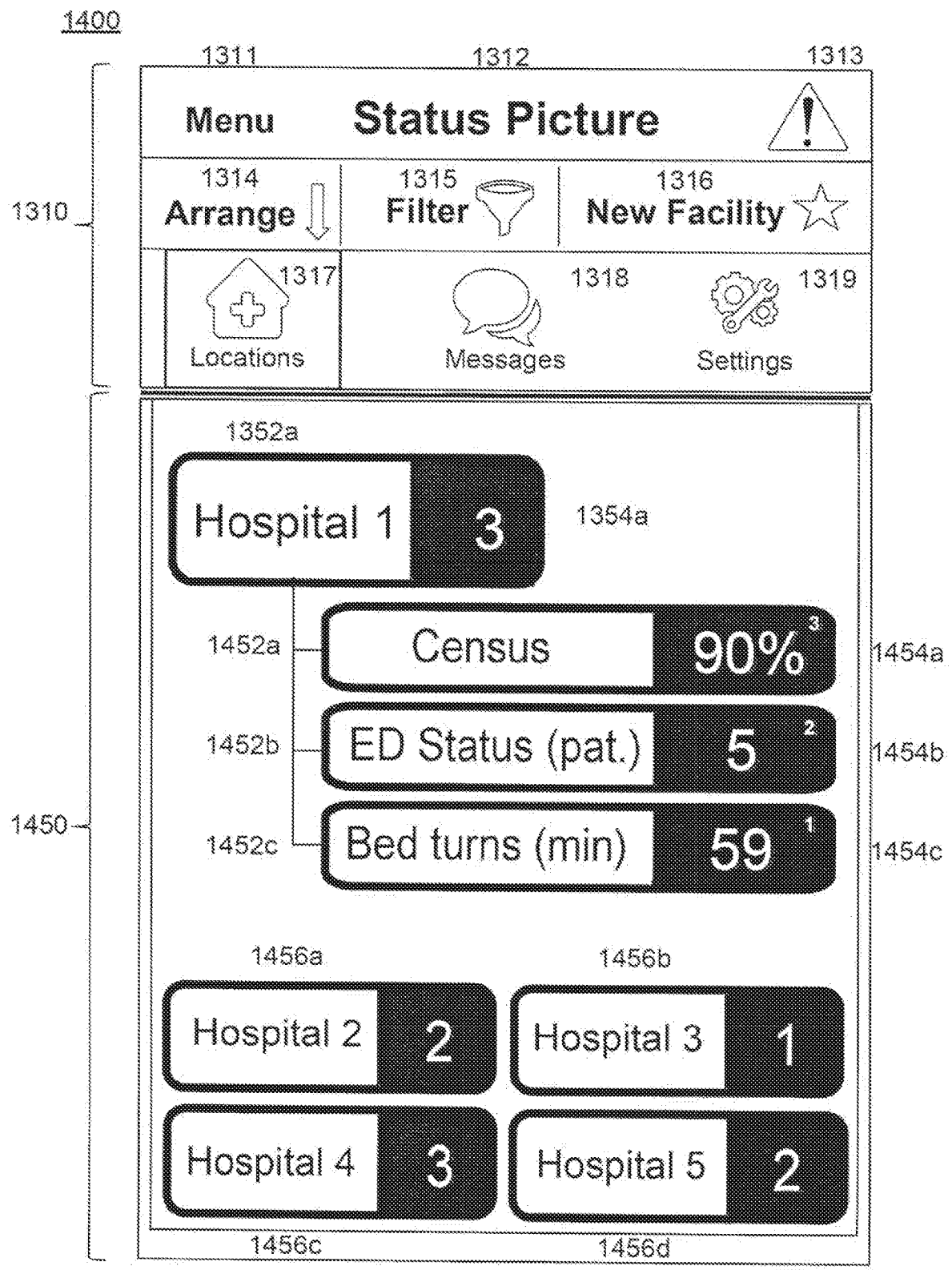
FIG. 14 is an illustration of an exemplary graphical user interface 1400 with secondary graphical objects, consistent with the disclosed embodiments.

FIG. 14 is an illustration of an exemplary graphical user interface with secondary graphical objects, consistent with the disclosed embodiments. User device 102 may display interface 1400 after processor 530 receives a request for secondary graphical objects and renders graphical objects based on a subset of information. For example interface 1400 may be displayed in step 1220 and after user 104 clicks in a primary graphical object displayed in interface 1300.

Interface 1400 may replicate status bar 1320, task bar 1321, and navigation bar 1322. It may replicate them in the same positions as in interface 1300 or it may change the positioning of bars to top, bottom, or side edges. Interface 1400, may include a combination of primary objects 1352, modified primary objects 1456, and secondary objects 1452 in secondary body section 1450. For example, FIG. 14 shows a primary object with portions 1352a and 1354a (as previously presented in FIG. 13). However, secondary body section 1450 may also include secondary objects. Similarly to the primary objects, secondary objects may be divided in different parts. For example, a secondary object may have secondary label 1452, and secondary attribute 1454. Different graphical styles can be applied to each part of the object. In some embodiments, secondary attribute may replicate the icons, color codes, or numbers described for the primary object. However, in some embodiments secondary attribute 1454 may additionally include information of the variable associated to the secondary object. For example, attribute may include the specific census or bed turns associated with the first object. In addition, secondary objects may include a color code for each one of the secondary objects. Secondary body section 1450 may also include modified primary objects. In some embodiments, primary objects that are not included in those selected in a request for additional information may be eliminated from interface 1400. However, as shown in FIG. 14, non-selected primary objects may also be modified and remain in display 510. For example, the size of non-selected primary objects may be reduced, or the style of non-selected primary objects maybe modified to indicate that they were not selected (see, e.g., FIG. 12). Then, modified primary objects 1456 present an exemplary embodiment for primary elements in the secondary interface 1400.

Figure 15A:
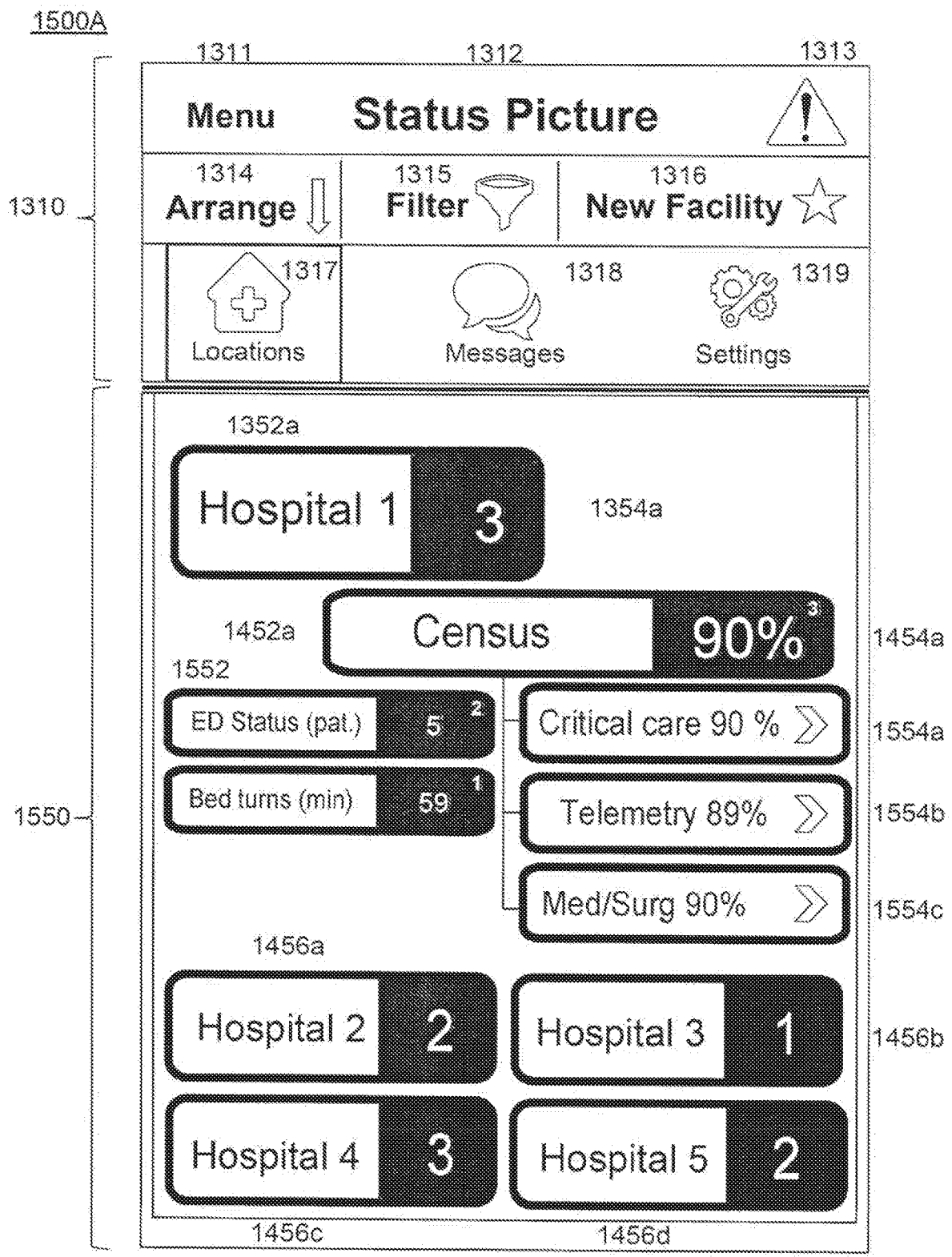
FIGS. 15A-15C are illustrations of exemplary graphical user interfaces 1500A-1500C, respectively, with tertiary graphical objects, consistent with the disclosed embodiments.
Figure 15:
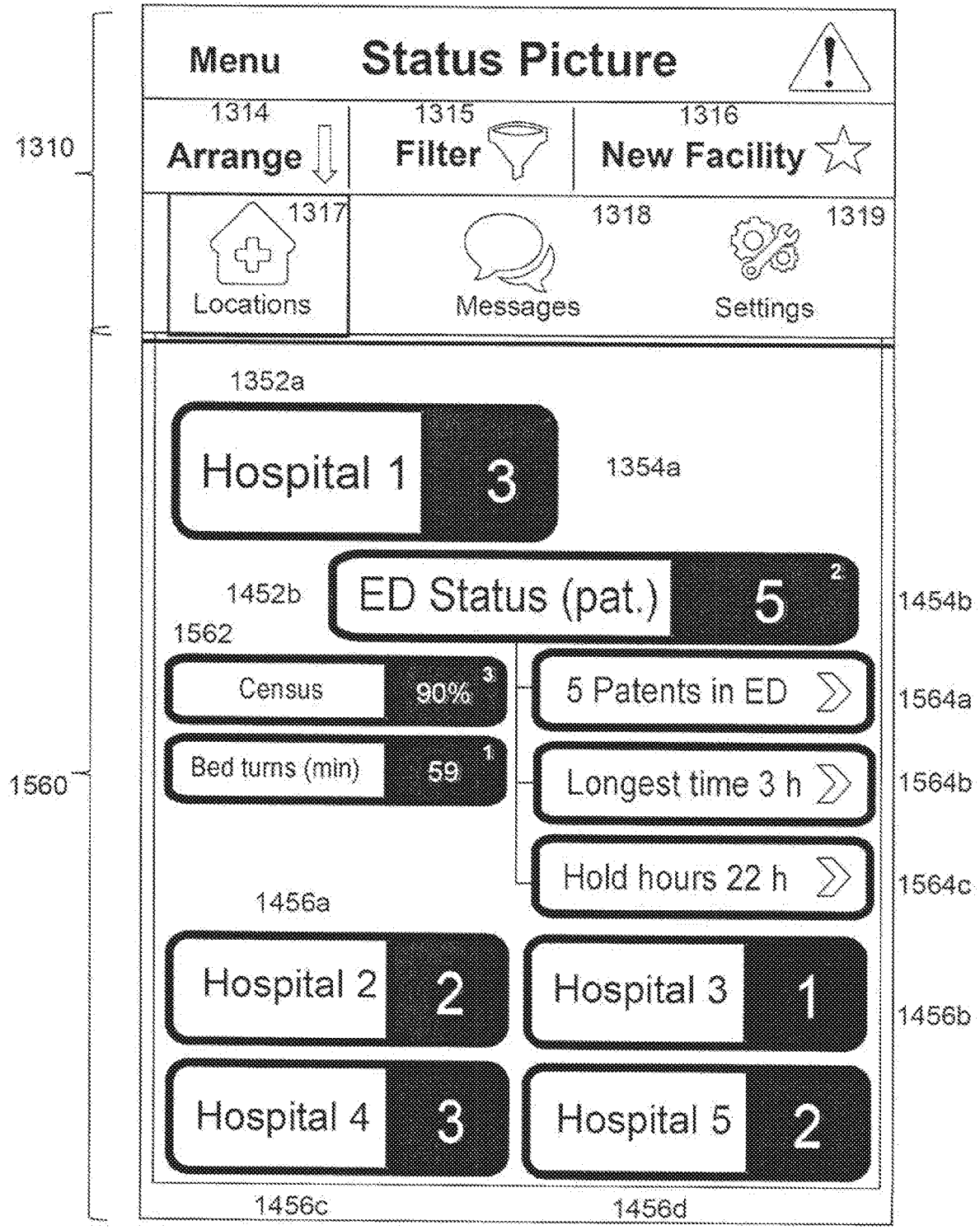
Figure 15:
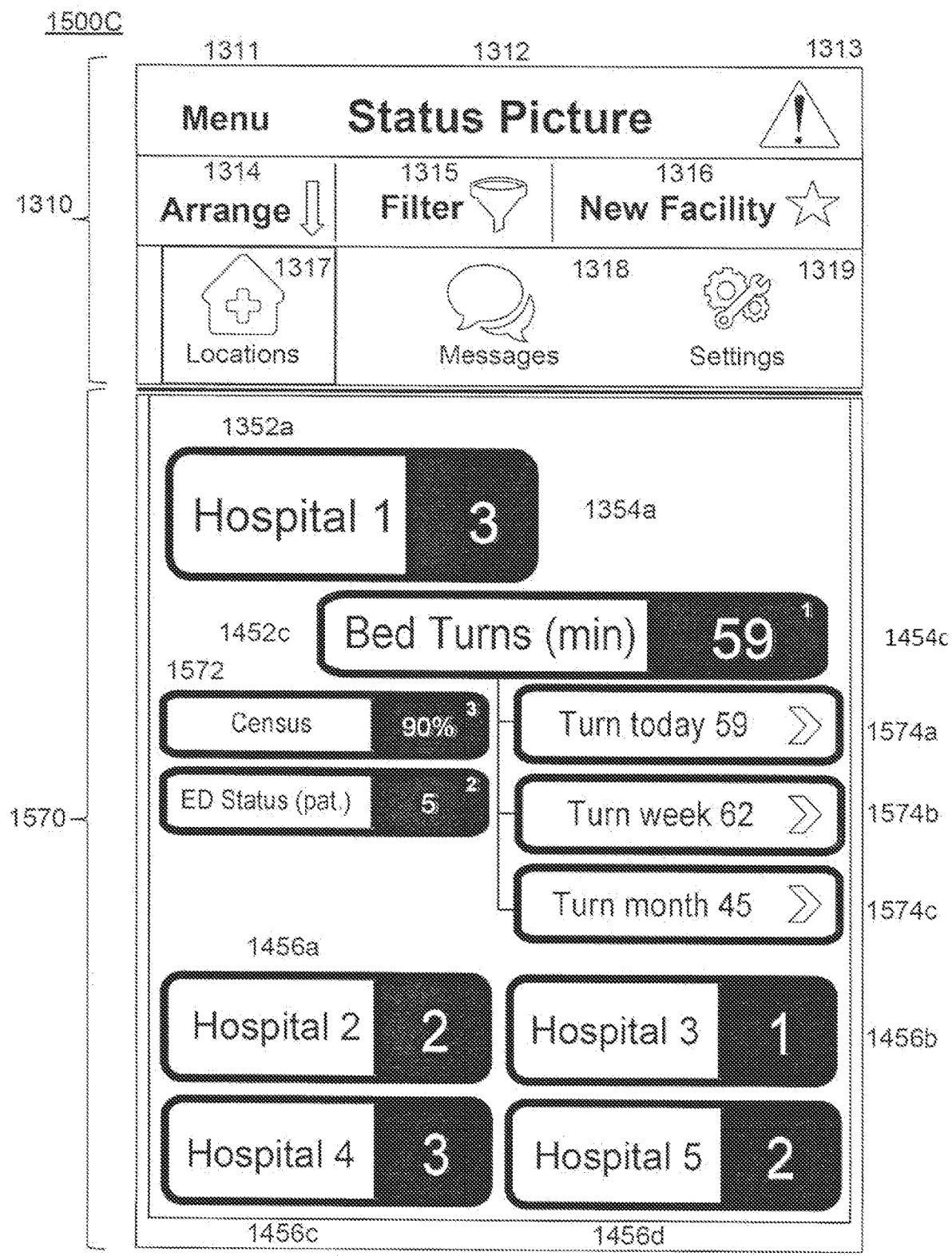

FIGS. 15A-15C are illustrations of exemplary graphical user interfaces with tertiary graphical objects, consistent with the disclosed embodiments. User device 102 may display interface 1500A, 1500B, or 1500C after processor 530 receives a request for tertiary graphical objects and renders additional graphical objects based on subset information associated with a selected secondary graphical object using routines such as process 1200. Interface 1500A may be, for example, display in step 1220. After user 104 clicks or interacts with a secondary graphical object.

Interfaces 1500 may replicate status bar 1320, task bar 1321, and navigation bar 1322. It may replicate them in the same positions as in interface 1300 or it may change the positioning of bars to top, bottom, or side edges. Interfaces 1500, however, may include a combination of primary objects 1352, modified primary objects 1456, secondary objects 1452, modified secondary objects 1552, and tertiary objects 1554 in tertiary body section 1550. For example, FIG. 15A show a primary object with portions 1352a and 1354a (as previously presented in FIG. 13), the modified primary objects 1456 and secondary object 1452 (as previously presented in FIG. 14). However, tertiary body section 1550 may also include modified secondary objects 1552, and tertiary graphical objects 1554. The tertiary objects may have a plurality of sections, as the primary and secondary objects, but may also have a single element with label and attribute in a single portion. Tertiary elements 1554a-c may display specific information the secondary graphical object. For example, if a secondary graphical object includes hospital census information, an associated tertiary graphical object may display census of a specific unit within the hospital. In addition, the tertiary object may include buttons associated with hypermedia elements to communicate or display different GUIs. For example, a button a critical care tertiary graphical object may call the intensive critical care unit direction. Also, a button in med/surg tertiary graphical object may display the following appointments in a calendar GUI. In addition, tertiary body section 1550 may include modified secondary objects 1552 which may replicate secondary objects of FIG. 14 but have modified size, style, or content when they are non-selected.

FIGS. 15B and 15C presents also interface 1500 but for a different selection of the secondary object within tertiary body section 1560 and 1570, respectively. These interfaces also have the same composition of primary, secondary and tertiary graphical objects (1564a-c and 1574a-c, respectively) and modified primary and secondary graphical objects (1562 and 1572, respectively) with a different selection of secondary object. They also present the tertiary objects with a single portion and buttons to available actions.

Figure 16:
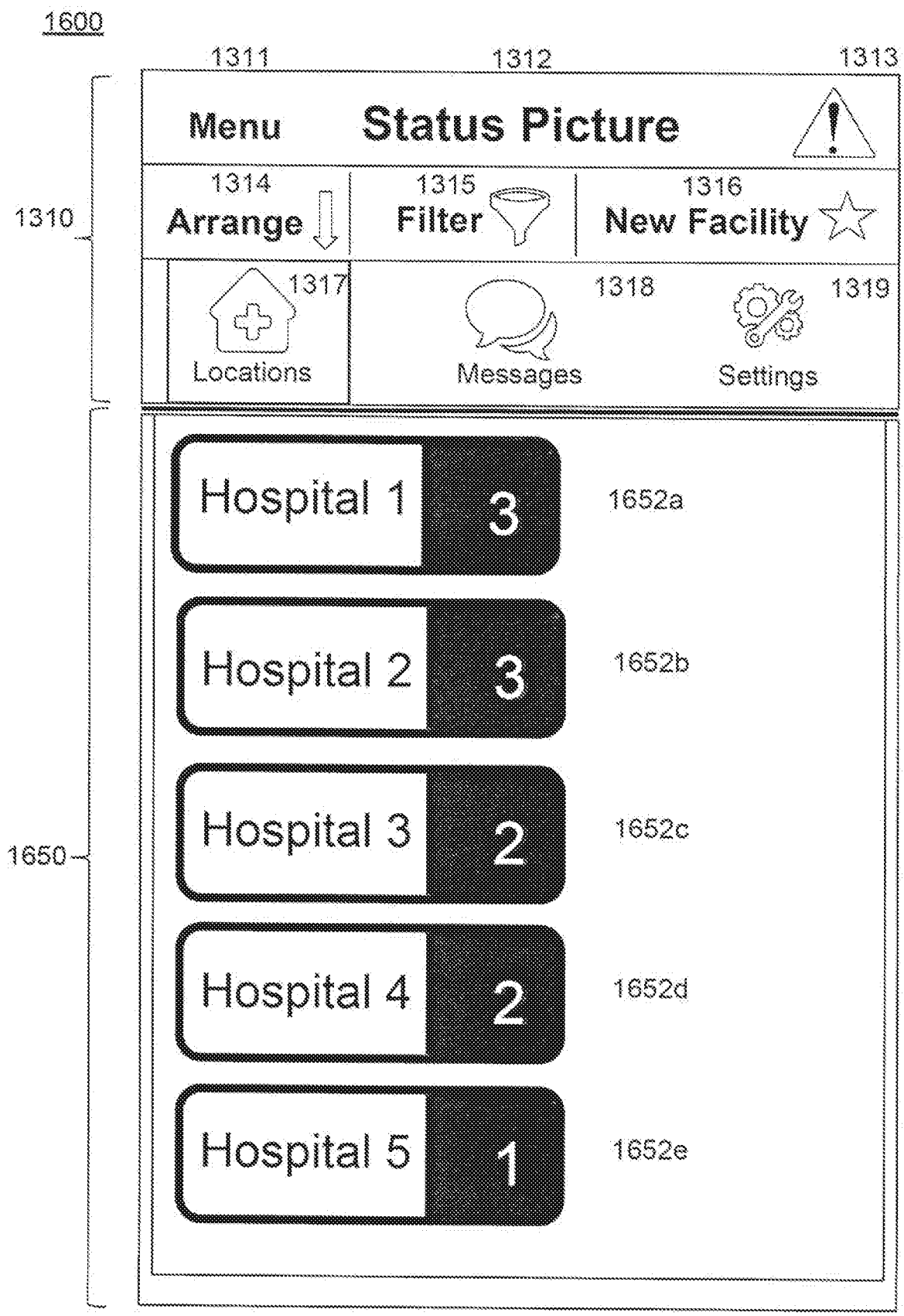
FIG. 16 is an illustration of an exemplary graphical user interface 1600 with organized primary graphical objects, according to disclosed embodiments.

FIG. 16 is an illustration of an exemplary graphical user interface with organized primary graphical objects, according to disclosed embodiments. User device 102 may display interface 1600 after processor 530 receives a request to arrange elements by, for example, user 104 clicking arrange button 1314. Interface 1600 presents only primary objects 1652a-e in the arranged body section 1650, but similar embodiments may include objects of different hierarchies.

Processor 530 may organize sort primary objects in arranged body section 1650 based on a sort value. In some embodiments, the sort value may be associated with the scoring variable. For example, graphical objects with the lowest score may be displayed on the top. In other embodiments, the sort value may be associated with the attributes of the graphical object. For example, as displayed in FIG. 16, arrange button 1314 may change the positon of primary graphical objects so the highest attribute is on top. In yet other embodiments, the sort value may be based on the label information. For example, processor 530 may do alphabetical arrangements of the objects based on their identifiers.

Figure 17:
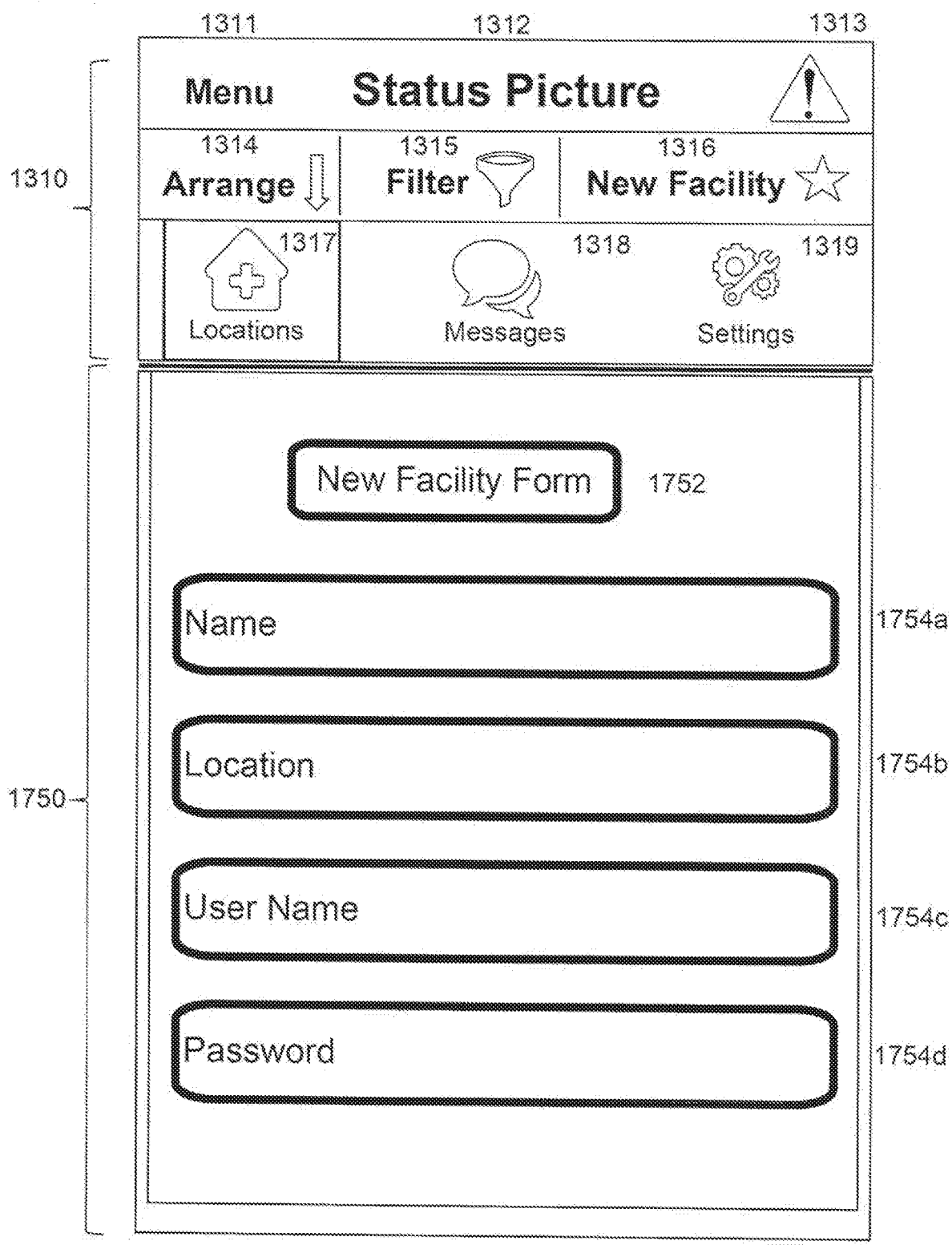
FIG. 17 is an illustration of an exemplary graphical user interface 1700 with a new facility form, consistent with disclosed embodiments.

FIG. 17 is an illustration of an exemplary graphical user interface with a new facility form, consistent with disclosed embodiments. User device 102 may display interface 1700 after processor 530 receives a request for a new facility. For example, user 104 may click button 1316 to include a new facility and as response processor 530 may generate interface 1700.

Interface 1700 may replicate status bar 1320, task bar 1321, and navigation bar 1322. It may replicate them in the same positions as in interface 1300 or it may change the positioning of bars to top, bottom, or side edges. Interface 1700, however, may include a new facility section 1750. For example, FIG. 17 shows an example of a new facility section 1750 which includes a title graphical object 1752 and input fields 1754. The input fields 1754 may include a label and an input section. The input sections may be text boxes, dials, or other graphical objects that allow the user to enter information. Input fields 1754 may include identifying information of a facility, such as name, address, phone, or other unique identifier. Additionally, the input fields 1754 may include authentication data information so user 104 can access information of the new facility.

The foregoing description has been presented for purposes of illustration. It is not exhaustive and is not limited to the precise forms or embodiments disclosed. Modifications and adaptations of the embodiments will be apparent from consideration of the specification and practice of the disclosed embodiments. For example, the described implementations include hardware, firmware, and software, but systems and methods consistent with the present disclosure can be implemented as hardware alone.

Computer programs based on the written description and methods of this specification are within the skill of a software developer. The various programs or program modules can be created using a variety of programming techniques. For example, program sections or program modules can be designed in or by means of Java, C, C++, assembly language, or any such programming languages. One or more of such software sections or modules can be integrated into a computer system, non-transitory computer readable media, or existing communications software.

Moreover, while illustrative embodiments have been described herein, the scope includes any and all embodiments having equivalent elements, modifications, omissions, combinations (e.g., of aspects across various embodiments), adaptations or alterations based on the present disclosure. Further, the steps of the disclosed methods can be modified in any manner, including by reordering steps or inserting or deleting steps.

What is claimed is:

1. A system comprising:
one or more processors; and
one or more storage devices storing instructions that, when executed, configure the one or more processors to:
transmit, to a mobile device in response to receiving a request to display a primary status of at least one hospital, instructions for displaying a first graphical user interface, the first graphical user interface comprising a first body and a header, the first body comprising a plurality of primary hypermedia elements each associated with the at least one hospital, each of the plurality of primary hypermedia elements being displayed with a graphical style determined based on a score of the at least one hospital corresponding to each of the primary hypermedia elements, wherein the graphical styles comprise a poor classification style comprising red color fonts and orange background and an above threshold classification style comprising green color fonts and blue background;
receive, from the mobile device, a reconfiguration request to modify at least one threshold associated with at least one of the plurality of primary hypermedia elements;
identify, from the plurality of primary hypermedia elements, those hypermedia elements having modifiable thresholds;
transmit, to the mobile device, instructions for displaying a second graphical user interface comprising the hypermedia elements having the modifiable thresholds in an object style different from those hypermedia elements not having the modifiable thresholds, the second graphical user interface being superimposed over the first body;
receive, from the mobile device, threshold modifications within the second graphical user interface;
modify threshold rules for a hospital corresponding to a hypermedia element having a received threshold modification; and
transmit, to the mobile device, instructions for displaying a third graphical user interface comprising the header and a second body, the second body comprising the plurality of primary hypermedia elements with modified graphical styles based upon the threshold rule modifications.

2. The system of claim 1, wherein the graphical styles comprise a color-coded attribute icon and one edge displaying the same color as the attribute icon.

3. The system of claim 1, wherein the instructions further configure the one or more processors to:
receive, from the mobile device, a request to display a secondary status associated with one of the plurality of primary hypermedia elements;
generate instructions for displaying a fourth graphical user interface in response to the request to display the secondary status, the fourth graphical user interface comprising the header and a third body, the third body comprising:
the plurality of primary hypermedia elements with an adjusted location, size, and content; and
a plurality of secondary hypermedia elements, displaying data associated with a hospital corresponding to the one of the plurality of primary hypermedia elements; and
transmit, to the mobile device, the instructions for displaying the fourth graphical user interface.

4. The system of claim 3, wherein the instructions further configure the one or more processors to:
determine whether the plurality of secondary hypermedia elements are associated with actions; and
in response to determining the plurality of secondary hypermedia elements are not associated with the actions,
transmit instructions for displaying an idle graphical user interface over the third body, the idle graphical user interface comprising warnings and recommendations and turning dark rest of the user interface screen.

5. The system of claim 4, wherein the instructions further configure the one or more processors to:
in response to determining the plurality of secondary hypermedia elements are associated with the actions, transmit instructions for displaying buttons associated with the plurality of secondary hypermedia elements, the buttons being displayed in a vicinity of the one of the plurality of primary hypermedia elements.

6. The system of claim 3, wherein the plurality of secondary hypermedia elements display a census, a number of bed turns, and an emergency department status associated with the hospital corresponding to the one of the plurality of primary hypermedia elements.

7. The system of claim 3, wherein the instructions further configure the one or more processors to:
receive, from the mobile device, a request to display a tertiary status associated with one of the plurality of secondary hypermedia elements;
generating instructions for displaying a fifth graphical user interface in response to the request to display the tertiary status, the fifth graphical user interface comprising the header and a fourth body, the fourth body comprising:
the plurality of primary hypermedia elements with a reduced size and content;
the plurality of secondary hypermedia elements; and
a plurality of tertiary hypermedia elements displaying data associated with the one of the plurality of secondary hypermedia elements; and
transmit, to the mobile device, the instructions for displaying the fifth graphical user interface.

8. The system of claim 7, wherein the plurality of tertiary hypermedia elements display at least one of a plurality of hospital unit census information, number of patients in emergency care, or weekly bed turnover rate.

9. The system of claim 7, wherein at least one of the plurality of tertiary hypermedia elements comprises a hyperlink to launch a messaging application.

10. The system of claim 1, wherein: the header comprises a status bar, a task bar, and a navigation bar; the status bar comprises a menu icon, a status message, and a status icon; the task bar comprises an arrange button, a filter button, and a new hospital button; and the navigation bar comprises a hospitals button, a messages button, and a settings button.

11. The system of claim 10, wherein a call to an action of the task bar generates the reconfiguration request.

12. The system of claim 1, further comprising selection objects to modify the thresholds, wherein the selection objects comprise at least one of dials, input boxes, or sliding bars.

13. The system of claim 1, wherein the instructions further configure the one or more processors to:
receive, from the mobile device, a request to add a new hospital to the plurality of primary hypermedia elements;
transmit, to the mobile device, instructions to display a fourth graphical user interface, the fourth graphical user interface comprising the header and a fourth body, the fourth body comprising an input form;
receive, from the mobile device, new hospital information within the input form of the fourth graphical user interface;
contact a server to determine whether the new hospital information matches hospitals associated with the system; and
in response to determining the new hospital information matches the hospitals associated with the system, generate a new primary hypermedia element based on the new hospital information.

14. The system of claim 13, wherein the instructions further configure the one or more processors to:
in response to determining the new hospital information does not match the hospitals associated with the system, transmit instructions for displaying a fifth graphical user interface, the fifth graphical user interface comprising a graphical object with an error message.

15. The system of claim 13, wherein the input form comprises a hospital name field and a hospital location field.

16. The system of claim 15, wherein the input form further comprises a user name field and a password field.

17. The system of claim 1, wherein: the one or more processors are coupled to an index server; and the index server is coupled to a plurality of hospital systems.

18. A non-transitory computer-readable medium storing instructions that, when executed by a processor, cause the processor to:

transmit, to a mobile device in response to receiving a request to display a primary status of at least one hospital, instructions for displaying a first graphical user interface, the first graphical user interface comprising a first body and a header, the first body comprising a plurality of primary hypermedia elements each associated with the at least one hospital, each of the plurality of primary hypermedia elements being displayed with a graphical style determined based on a score of the at least one hospital corresponding to each of the primary hypermedia elements, wherein the graphical styles comprise a poor classification style comprising red color fonts and orange background and an above threshold classification style comprising green color fonts and blue background;
receive, from the mobile device, a reconfiguration request to modify at least one threshold associated with at least one of the plurality of primary hypermedia elements;
identify, from the plurality of primary hypermedia elements, those hypermedia elements having modifiable thresholds;
transmit, to the mobile device, instructions for displaying a second graphical user interface comprising the hypermedia elements having the modifiable thresholds in an object style different from those hypermedia elements not having the modifiable thresholds, the second graphical user interface being superimposed over the first body;
receive, from the mobile device, threshold modifications within the second graphical user interface;
modify threshold rules for a hospital corresponding to a hypermedia element having a received threshold modification; and
transmit, to the mobile device, instructions for displaying a third graphical user interface comprising the header and a second body, the second body comprising the plurality of primary hypermedia elements with modified graphical styles based upon the threshold rule modifications.

19. A computer-implemented method comprising:
transmitting, to a mobile device in response to receiving a request to display a primary status of at least one hospital, instructions for displaying a first graphical user interface, the first graphical user interface comprising a first body and a header, the first body comprising a plurality of primary hypermedia elements each associated with the at least one hospital, each of the plurality of primary hypermedia elements being displayed with a graphical style determined based on a score of the at least one hospital corresponding to ene each of the primary hypermedia element, wherein the graphical styles comprise a poor classification style comprising red color fonts and orange background and an above threshold classification style comprising green color fonts and blue background;
receiving, from the mobile device, a reconfiguration request to modify at least one threshold associated with at least one of the plurality of primary hypermedia elements;
identifying, from the plurality of primary hypermedia elements, those hypermedia elements having modifiable thresholds;
transmitting, to the mobile device, instructions for displaying a second graphical user interface comprising the hypermedia elements having the modifiable thresholds in an object style different from those hypermedia elements not having the modifiable thresholds, the second graphical user interface being superimposed over the first body;

receiving, from the mobile device, threshold modifications within the second graphical user interface;

modifying threshold rules for a hospital corresponding to a hypermedia element having a received threshold modification; and transmitting, to the mobile device, instructions for displaying a third graphical user interface comprising the header and a second body, the second body comprising the plurality of primary hypermedia elements with modified graphical styles based upon the threshold rule modifications.

\* \* \* \* \*